United States Patent
Lucisano et al.

(10) Patent No.: US 10,561,351 B2
(45) Date of Patent: Feb. 18, 2020

(54) TISSUE IMPLANTABLE SENSOR WITH HERMETICALLY SEALED HOUSING

(75) Inventors: Joseph Y. Lucisano, San Diego, CA (US); Mark B. Catlin, Lake Oswego, OR (US); William J. Choi, San Diego, CA (US); Payton C. Chu, San Diego, CA (US); Joe T. Lin, San Diego, CA (US); Timothy L. Routh, San Diego, CA (US); Thomas G. Wallner, San Marcos, CA (US)

(73) Assignee: GLYSENS INCORPORATED, San Diego, CA (US)

( * ) Notice: Subject to any disclaimer, the term of this patent is extended or adjusted under 35 U.S.C. 154(b) by 624 days.

(21) Appl. No.: 13/559,475

(22) Filed: Jul. 26, 2012

(65) Prior Publication Data
US 2013/0197332 A1 Aug. 1, 2013

Related U.S. Application Data

(60) Provisional application No. 61/511,930, filed on Jul. 26, 2011.

(51) Int. Cl.
*A61B 5/1473* (2006.01)
*A61B 5/00* (2006.01)
(Continued)

(52) U.S. Cl.
CPC .......... *A61B 5/1473* (2013.01); *A61B 5/0031* (2013.01); *A61B 5/076* (2013.01);
(Continued)

(58) Field of Classification Search
CPC ... A61B 5/1473; A61B 5/076; A61B 5/14542; A61B 5/14546; A61B 2562/04;
(Continued)

(56) References Cited

U.S. PATENT DOCUMENTS 2,508,523 A 5/1950 Krebs
2,563,062 A 8/1951 Perley
(Continued)

FOREIGN PATENT DOCUMENTS

CN 1355670 A 6/2002
CN 1592570 A 3/2005
(Continued)

OTHER PUBLICATIONS

Armour et al. "Application of chronic intravascular blood glucose sensor in dogs," Diabetes 39, 1519-1526 (1990).
(Continued)

*Primary Examiner* — Tiffany Weston
(74) *Attorney, Agent, or Firm* — Gazdzinski & Associates, PC

(57) ABSTRACT

A tissue-implantable sensor for measurement of solutes in fluids and gases, such as oxygen and glucose, is provided. The sensor includes: i) a detector array including at least one detector; ii) a telemetry transmission portal; iii) an electrical power source; and iv) circuitry electrically connected to the detector array including signal processing means for determining an analyte level, such as glucose level, in a body fluid contacting the detectors. The sensor components are disposed in a hermetically sealed housing having a size and shape suitable for comfortable, safe, and unobtrusive subcutaneous implantation allowing for in vivo detection and long term monitoring of tissue glucose concentrations by wireless telemetry.

31 Claims, 18 Drawing Sheets

(51) Int. Cl.
  *A61B 5/07* (2006.01)
  *A61B 5/145* (2006.01)
  *A61B 5/1486* (2006.01)

(52) U.S. Cl.
  CPC ...... *A61B 5/14532* (2013.01); *A61B 5/14542* (2013.01); *A61B 5/14865* (2013.01); *A61B 5/14546* (2013.01); *A61B 2562/0209* (2013.01); *A61B 2562/04* (2013.01); *Y10T 29/49117* (2015.01); *Y10T 29/49826* (2015.01)

(58) Field of Classification Search
  CPC .......... A61B 2562/0209; A61B 5/0031; A61B 5/14532; A61B 5/14865; Y10T 29/49117; Y10T 29/49826
  USPC .......................................... 600/345, 347, 365
  See application file for complete search history.

(56) References Cited

U.S. PATENT DOCUMENTS

| | | |
|---|---|---|
| 2,805,191 A | 9/1957 | Hersch |
| 2,864,750 A | 12/1958 | Hughes, Jr. et al. |
| 2,998,371 A | 8/1961 | Sabins |
| 3,099,575 A | 7/1963 | Hill |
| 3,246,235 A | 4/1966 | Allsopp |
| 3,249,250 A | 5/1966 | McKee |
| 3,300,345 A | 1/1967 | Lyons, Jr. |
| 3,308,046 A | 3/1967 | Suleski |
| 3,458,421 A | 7/1969 | Dahms |
| 3,505,195 A | 4/1970 | Borge et al. |
| 3,542,662 A | 11/1970 | Hicks et al. |
| 3,616,412 A | 10/1971 | Gnage |
| 3,957,613 A | 5/1976 | Macur |
| 4,036,716 A | 7/1977 | Hulthe |
| 4,088,550 A | 5/1978 | Malkin |
| 4,240,438 A | 12/1980 | Shults et al. |
| 4,306,952 A | 12/1981 | Jansen |
| 4,340,457 A | 7/1982 | Kater |
| 4,361,153 A | 11/1982 | Slocum et al. |
| 4,366,033 A | 12/1982 | Richter et al. |
| 4,431,004 A | 2/1984 | Bessman et al. |
| 4,458,686 A | 7/1984 | Clark, Jr. |
| 4,484,987 A | 11/1984 | Gough |
| 4,494,950 A | 1/1985 | Fischell |
| 4,541,431 A | 9/1985 | Ibrahim et al. |
| 4,550,732 A | 11/1985 | Batty, Jr. et al. |
| 4,553,547 A | 11/1985 | Keimel |
| 4,571,589 A | 2/1986 | Slocum et al. |
| 4,637,861 A | 1/1987 | Krull et al. |
| 4,650,547 A | 3/1987 | Gough |
| 4,671,288 A | 6/1987 | Gough |
| 4,703,756 A | 11/1987 | Gough et al. |
| 4,746,218 A | 5/1988 | Lord, III |
| 4,748,562 A | 5/1988 | Miller et al. |
| 4,759,828 A | 7/1988 | Young et al. |
| 4,781,798 A | 11/1988 | Gough |
| 4,830,713 A | 5/1989 | Gagescu |
| 4,890,620 A | 1/1990 | Gough |
| 5,042,902 A | 8/1991 | Huebscher et al. |
| 5,046,242 A | 9/1991 | Kuzma |
| 5,077,476 A | 12/1991 | Rosenthal |
| 5,105,811 A | 4/1992 | Kuzma |
| 5,112,455 A | 5/1992 | Cozzette et al. |
| 5,150,516 A | 9/1992 | Boero et al. |
| 5,165,406 A | 11/1992 | Wong |
| 5,189,717 A | 2/1993 | Larson et al. |
| 5,264,103 A | 11/1993 | Yoshioka et al. |
| 5,272,283 A | 12/1993 | Kuzma |
| 5,273,203 A | 12/1993 | Webster |
| 5,283,104 A | 2/1994 | Aoude et al. |
| 5,283,204 A | 2/1994 | Rhodes et al. |
| 5,284,140 A | 2/1994 | Allen et al. |
| 5,322,063 A | 6/1994 | Allen |
| 5,337,475 A | 8/1994 | Aoude et al. |
| 5,395,504 A | 3/1995 | Saurer et al. |
| 5,431,160 A | 7/1995 | Wilkins |
| 5,487,855 A | 1/1996 | Moeggenborg et al. |
| 5,497,772 A | 3/1996 | Schulman |
| 5,560,098 A | 10/1996 | Robins |
| 5,660,163 A | 8/1997 | Schulman |
| 5,692,299 A | 12/1997 | Daems et al. |
| 5,695,623 A | 12/1997 | Michel et al. |
| 5,711,861 A | 1/1998 | Ward |
| 5,727,283 A | 3/1998 | Webster |
| 5,741,330 A | 4/1998 | Brauker et al. |
| 5,750,926 A | 5/1998 | Schulman et al. |
| 5,776,324 A | 7/1998 | Usala |
| 5,777,060 A | 7/1998 | Van Antwerp |
| 5,782,755 A | 7/1998 | Chance et al. |
| 5,782,891 A | 7/1998 | Hassler et al. |
| 5,791,344 A | 8/1998 | Schulman |
| 5,804,048 A | 9/1998 | Wong et al. |
| 5,821,011 A | 10/1998 | Taylor et al. |
| 5,842,983 A * | 12/1998 | Abel ..................... C12Q 1/001 204/403.1 |
| 5,855,995 A | 1/1999 | Haq et al. |
| 5,864,088 A * | 1/1999 | Sato ..................... H01L 23/552 174/386 |
| 5,882,494 A | 3/1999 | Van Antwerp |
| 5,887,240 A | 3/1999 | Fournier et al. |
| 5,932,175 A | 8/1999 | Knute et al. |
| 5,942,842 A | 8/1999 | Fogle, Jr. |
| 5,964,993 A | 10/1999 | Blubaugh, Jr. et al. |
| 5,985,129 A | 11/1999 | Gough et al. |
| 6,001,067 A | 12/1999 | Shults |
| 6,027,479 A | 2/2000 | Alei et al. |
| 6,041,496 A | 3/2000 | Haq et al. |
| 6,081,736 A * | 6/2000 | Colvin ............... A61B 5/14865 600/347 |
| 6,090,503 A | 7/2000 | Taylor et al. |
| 6,096,066 A | 8/2000 | Chen et al. |
| 6,107,083 A | 8/2000 | Collins et al. |
| 6,119,208 A | 9/2000 | White et al. |
| 6,193,421 B1 | 2/2001 | Tamekuni et al. |
| 6,200,772 B1 | 3/2001 | Vadgama et al. |
| 6,212,416 B1 | 4/2001 | Ward |
| 6,221,513 B1 | 4/2001 | Lasater |
| 6,403,944 B1 | 6/2002 | MacKenzie et al. |
| 6,466,810 B1 | 10/2002 | Ward |
| 6,516,808 B2 | 2/2003 | Schulman |
| 6,551,252 B2 | 4/2003 | Sackner et al. |
| 6,558,321 B1 | 5/2003 | Burd et al. |
| 6,642,015 B2 | 11/2003 | Vachon et al. |
| 1,301,051 A1 | 1/2004 | Tagi et al. |
| 6,721,587 B2 | 4/2004 | Gough |
| 6,741,877 B1 | 5/2004 | Shults |
| 6,809,607 B2 | 10/2004 | Nagasaka |
| 6,812,404 B1 | 11/2004 | Martinez |
| 6,832,114 B1 | 12/2004 | Whitehurst et al. |
| 6,843,107 B2 | 1/2005 | Newman et al. |
| 6,931,268 B1 | 8/2005 | Kiani-Azarbayjany et al. |
| 7,005,796 B2 | 2/2006 | Kolluri et al. |
| 7,079,881 B2 | 7/2006 | Schulman |
| 7,106,939 B2 | 9/2006 | Labrake et al. |
| 7,110,803 B2 | 9/2006 | Shults |
| 7,134,999 B2 | 11/2006 | Brauker |
| 7,136,689 B2 | 11/2006 | Shults |
| 7,140,787 B2 | 11/2006 | Yamauchi et al. |
| 7,146,203 B2 | 12/2006 | Botvinick et al. |
| 7,161,727 B2 | 1/2007 | Callies et al. |
| 7,189,341 B2 | 3/2007 | Li et al. |
| 7,226,978 B2 | 6/2007 | Tapsak et al. |
| 7,248,912 B2 * | 7/2007 | Gough ................ A61B 5/0031 600/316 |
| 7,323,142 B2 | 1/2008 | Pendo et al. |
| 7,336,984 B2 * | 2/2008 | Gough ............... A61B 5/14532 600/345 |
| 7,460,898 B2 | 12/2008 | Brister |
| 7,467,003 B2 | 12/2008 | Brister |
| 7,471,972 B2 | 12/2008 | Rhodes |
| 7,480,988 B2 | 1/2009 | Ok et al. |
| 7,497,827 B2 | 3/2009 | Brister et al. |
| 7,514,791 B2 | 4/2009 | Shah et al. |

(56) References Cited

U.S. PATENT DOCUMENTS

| | | |
|---|---|---|
| 7,525,298 B2 | 4/2009 | Morgan |
| 7,761,130 B2 | 7/2010 | Simpson |
| 7,857,760 B2 | 12/2010 | Brister et al. |
| 7,871,456 B2 | 1/2011 | Gough et al. |
| 7,875,293 B2 | 1/2011 | Shults et al. |
| 7,881,763 B2 | 2/2011 | Brauker |
| 7,894,870 B1* | 2/2011 | Lucisano ............... G01N 27/12 600/345 |
| 8,133,178 B2 | 3/2012 | Brauker et al. |
| 8,270,661 B2 | 9/2012 | Sorensen et al. |
| 8,357,107 B2 | 1/2013 | Draudt et al. |
| 8,690,820 B2 | 4/2014 | Cinar et al. |
| 8,763,245 B1 | 7/2014 | Lucisano et al. |
| 9,002,711 B2 | 4/2015 | Morinaka et al. |
| 9,119,528 B2 | 9/2015 | Cobelli et al. |
| 9,247,901 B2 | 2/2016 | Kamath et al. |
| 9,325,060 B2 | 4/2016 | Kalistaja et al. |
| 9,362,776 B2 | 6/2016 | Low et al. |
| 9,444,027 B2 | 9/2016 | Dibra et al. |
| 9,451,908 B2 | 9/2016 | Kamath et al. |
| 2002/0026108 A1 | 2/2002 | Colvin et al. |
| 2002/0123087 A1 | 9/2002 | Vachon et al. |
| 2002/0156355 A1 | 10/2002 | Gough |
| 2002/0161286 A1 | 10/2002 | Gerber et al. |
| 2002/0193671 A1 | 12/2002 | Ciurczak et al. |
| 2003/0048621 A1* | 3/2003 | Blood ................... H05K 1/189 361/785 |
| 2003/0049166 A1 | 3/2003 | Pendo et al. |
| 2003/0053784 A1 | 3/2003 | Labrake et al. |
| 2003/0126593 A1 | 7/2003 | Mault |
| 2003/0179167 A1 | 9/2003 | Kolluri et al. |
| 2003/0181794 A1 | 9/2003 | Rini et al. |
| 2003/0187338 A1 | 10/2003 | Say et al. |
| 2003/0217966 A1 | 11/2003 | Tapsak et al. |
| 2003/0228681 A1 | 12/2003 | Ritts et al. |
| 2004/0011671 A1 | 1/2004 | Shults et al. |
| 2004/0057043 A1 | 3/2004 | Newman et al. |
| 2004/0064133 A1 | 4/2004 | Miller et al. |
| 2004/0106857 A1 | 6/2004 | Gough et al. |
| 2004/0158194 A1 | 8/2004 | Wolff et al. |
| 2004/0167080 A1 | 8/2004 | Dodge et al. |
| 2004/0176669 A1 | 9/2004 | Colvin et al. |
| 2004/0190111 A1 | 9/2004 | Callies et al. |
| 2004/0199059 A1 | 10/2004 | Brauker et al. |
| 2004/0220459 A1 | 11/2004 | Schlegel et al. |
| 2005/0027175 A1 | 2/2005 | Yang |
| 2005/0031689 A1 | 2/2005 | Shults et al. |
| 2005/0033132 A1 | 2/2005 | Shults et al. |
| 2005/0052858 A1 | 3/2005 | Shima |
| 2005/0059871 A1 | 3/2005 | Gough et al. |
| 2005/0124873 A1 | 6/2005 | Shults et al. |
| 2005/0154271 A1* | 7/2005 | Rasdal ................ A61B 5/076 600/347 |
| 2005/0177036 A1 | 8/2005 | Shults et al. |
| 2005/0196322 A1 | 9/2005 | Truex et al. |
| 2005/0245799 A1 | 11/2005 | Brauker |
| 2005/0245971 A1* | 11/2005 | Brockway ............ A61N 1/3787 607/2 |
| 2005/0251083 A1 | 11/2005 | Carr-Brendel |
| 2005/0272989 A1* | 12/2005 | Shah ................... A61B 5/14532 600/345 |
| 2006/0085137 A1 | 4/2006 | Bartkowiak et al. |
| 2006/0086624 A1 | 4/2006 | Tapsak et al. |
| 2006/0195029 A1 | 8/2006 | Shults et al. |
| 2006/0204536 A1 | 9/2006 | Shults et al. |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2007/0151868 A1 | 7/2007 | Staib et al. |
| 2008/0033269 A1 | 2/2008 | Zhang |
| 2008/0033272 A1 | 2/2008 | Gough et al. |
| 2008/0039702 A1 | 2/2008 | Hayter et al. |
| 2008/0197024 A1 | 8/2008 | Simpson et al. |
| 2008/0200791 A1 | 8/2008 | Simpson et al. |
| 2008/0317276 A1 | 12/2008 | Sorensen et al. |
| 2009/0281399 A1* | 11/2009 | Keel ................. A61B 5/02158 600/301 |
| 2010/0041971 A1* | 2/2010 | Goode, Jr. ........... A61B 5/0031 600/345 |
| 2010/0145317 A1 | 6/2010 | Laster et al. |
| 2010/0149042 A1 | 6/2010 | Utsi et al. |
| 2011/0137142 A1 | 6/2011 | Lucisano et al. |
| 2012/0262298 A1 | 10/2012 | Bohm et al. |
| 2012/0283960 A1 | 11/2012 | Budiman |
| 2012/0323100 A1 | 12/2012 | Kamath et al. |
| 2013/0016573 A1 | 1/2013 | Goel et al. |
| 2013/0030273 A1 | 1/2013 | Tapsak et al. |
| 2013/0172692 A1 | 7/2013 | Choi et al. |
| 2013/0178727 A1 | 7/2013 | Hayter et al. |
| 2013/0197332 A1 | 8/2013 | Lucisano |
| 2014/0046148 A1 | 2/2014 | Simpson et al. |
| 2014/0309510 A1 | 10/2014 | Lucisano et al. |
| 2014/0323960 A1 | 10/2014 | Sloan |
| 2014/0350652 A1 | 11/2014 | Suwito |
| 2015/0163602 A1 | 6/2015 | Pedersen et al. |
| 2015/0250429 A1 | 9/2015 | Hampapuram et al. |
| 2015/0289823 A1 | 10/2015 | Rack-Gomer et al. |
| 2015/0335285 A1 | 11/2015 | Poon et al. |
| 2016/0022180 A1 | 1/2016 | Joseph et al. |
| 2016/0073964 A1 | 3/2016 | Cobelli et al. |
| 2016/0134980 A1 | 5/2016 | Abolfathi |
| 2016/0163174 A1 | 6/2016 | Zhang et al. |
| 2016/0235300 A1 | 8/2016 | Goodnow |
| 2016/0317744 A1 | 11/2016 | Rule et al. |
| 2017/0173262 A1 | 6/2017 | Veltz |
| 2017/0181628 A1 | 6/2017 | Burnette et al. |
| 2017/0181630 A1 | 6/2017 | Mahalingam et al. |
| 2017/0181674 A1 | 6/2017 | Lucisano et al. |
| 2017/0325725 A1 | 11/2017 | Shah et al. |
| 2017/0347932 A1 | 12/2017 | Lucisano et al. |
| 2017/0357776 A1 | 12/2017 | Baker et al. |
| 2018/0000395 A1 | 1/2018 | Lucisano et al. |
| 2018/0140239 A1 | 5/2018 | Lucisano et al. |
| 2018/0153450 A1 | 6/2018 | Routh et al. |

FOREIGN PATENT DOCUMENTS

| | | |
|---|---|---|
| CN | 101006374 A | 7/2007 |
| CN | 201207090 Y | 3/2009 |
| EP | 0 852 414 B1 | 11/2004 |
| JP | H11295556 A | 10/1999 |
| JP | 2000121863 A | 4/2000 |
| JP | 2005308982 A | 11/2005 |
| JP | 2007121886 A | 5/2007 |
| WO | WO-9213271 A1 | 8/1992 |
| WO | WO 2008/013881 A2 | 1/2008 |
| WO | WO 2011/018407 | 2/2011 |
| WO | WO 2011/120014 A1 | 2/2011 |
| WO | WO-2014035672 A2 | 3/2014 |

OTHER PUBLICATIONS

Bremer, et al., "Benchmark data from the literature for evaluation of new glucose sensing technologies," Diabetes Technol. Ther., 3:409-418 (2001).

Choleau, et al., "Calibration of a subcutaneous amperometric glucose sensor implanted for 7 days in diabetic patients. Part 2. Superiority of the one-point calibration method," Biosens. Bioelectron., 17:647-654 (2002).

Choleau, et al., "Calibration of a subcutaneous amperometric glucose sensor. Part 1. Effect of measurement uncertainties on the determination of sensor sensitivity and background current,"Biosens. Bioelectron., 17:641-646 (2002).

Gough et al.,"Two-dimensional enzyme electrode sensor for glucose," Anal. Chem. 57(12):2351-2357 (1985).

Kovatchev et al., "Graphical and Numerical Evaluation of Continuous Glucose Sensing Time Lag" Diabetes Technol. Ther. 11, 139-143 (2009).

International Search Report regarding PCT/US2012/048397.

Japanese Office Action dated May 26, 2016, regarding JP 2014-523024.

(56) References Cited

OTHER PUBLICATIONS

Chinese Office Action dated Mar. 10, 2016, regarding 201280039622.4.
Japanese Office Action dated Apr. 3, 2017, regarding JP 2014-523024.
Alvarez-Icaza M., et al., "Mass Production of Biosensors," Analytical Chemistry, 1993, vol. 65 (11), pp. 525-533.
Anderson J.M., "Biological Responses to Materials." Annual Review of Materials Research, 2001, vol. 31, pp. 81-110.
Bard A.J., et al., "Electrochemical Methods: Fundamentals and Applications," 2nd Edition, 2000.
Bilitewski U., et al., "Glucose Biosensors Based on Thick Film Technology," Biosensors and Bioelectronics, 1991, vol. 6, pp. 369-373.
Cha, C.S., et al., "Electrochemical Behaviour of Microfabricated Thick-film Electrodes," Sensors and Actuators B., 1990, vol. 2, pp. 277-281.
Conway M.J., et al., "Radio Telemetry of Blood Po2 in Vivo," Biomedical Engineering, 1973, vol. 8 (10), pp. 428-430.
Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.
Dutronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.
Fischer U., et al., "A Membrane Combination for Implantable Glucose Sensors. Measurements in Undiluted Biological Fluids," Transactions—American Society for Artificial Internal Organs, 1982, vol. 28, pp. 245-248.
Golonka L.J., et al., "The influence of the Electrode Material on the Sensitivity of an Sno.sub.2 Thick-film Gas Sensor," Sensors and Actuators B, 1994, vol. 18-19, pp. 453-456.
Gough D.A., et al., "A Novel Rotated Disc Electrode and Time Lag Method for Characterizing Mass Transport in Liquid-membrane Systems," Journal of the American Institute of Chemical Engineers, 1980, vol. 26, pp. 1013.
Gough D.A., et al., "Membrane-covered, Rotated Disc Electrode," Analytical Chemistry, 1979, vol. 51, pp. 439-444.
Gough, et al., "Function of an Implanted Tissue Glucose Sensor for More than 1 Year in Animals", Science Translational Medicine, Jul. 28, 2010, vol. 2 (42), pp. 42ra53.
Holc J., et al., "Interaction Between Thick-film Platinum Electrodes and Yttria-stabilized Zro.sub.2 Ceramic," Journal of Materials Science Letters, 1989, vol. 8, pp. 635-637.
Holmes, et al., Handbook of Thick Film Technology, Electrochemical Publications Ltd (Glasgow: Bell and Bain Ltd., 1976).
Jablecki M., et al., "Simulations of the Frequency Response of Implantable Glucose Sensors," Analytical Chemistry, 2000, vol. 72 (8), pp. 1853-1859.
Kroschwitz J., "Concise encyclopedia of polymer science and engineering," John Wiley, 1990, pp. 599-1341.
Lemey S., et al., "Wearable Flexible Lightweight Modular RFID Tag With Integrated Energy Harvester," IEEE Transactions on Microwave Theory and Techniques, 2016, vol. 64.7, pp. 2304-2314.
Leypoldt J.K., et al., "Diffusion and the Limiting Substrate in Two-substrate Immobilized Enzyme Systems," Biotechnology and Bioengineering, 1982, vol. 24 (12), pp. 2705-2719.
Leypoldt J.K., et al., "Model of a Two-substrate Enzyme Electrode for Glucose," Analytical Chemistry, 1984, vol. 56 (14), pp. 2896-2904.
Lucisano, et al., "In Vitro Stability of an Oxygen Sensor," Analytical Chemistry, 1987, vol. 59 (5), pp. 736-739.
Lucisano, Ph.D. Dissertation, Univ. of Calif. (San Diego), pp. xv-xvi, 8-10, 26-30, 34-36, 96-97 (made available to the public on Dec. 15, 1988)—Call No. "T3.6.L821987".
Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.
Makale M.T., et al., "Tissue Window Chamber System for Validation of Implanted Oxygen Sensors," American Journal of Physiology. Heart and Circulatory Physiology, 2003, vol. 284 (6), pp. 2288-2294.
Mckean B.D., et al., "A Telemetry-Instrumentation System for Chronically Implanted Glucose and Oxygen Sensors," IEEE Transactions on Biomedical Engineering, 1988, vol. 35 (7), pp. 526-532.
Mcnaught A.D., et al., "The Compendium of Chemical Terminology," The Gold Book, Second Edition, Blackwell Science, 1997.
Rich A., "Shielding and Guarding," Analog Dialogue, 1983, vol. 17 (1), pp. 8-13.
Sargent B.J., et al., "Design and Validation of the Transparent Oxygen Sensor Array," Biomedical Engineering, IEEE Transactions on, 1991, vol. 38 (5), pp. 476-482.
Schultz J.S., et al., "Optical Fiber Affinity Sensors," Methods in Enzymology, K. Mosbach, Ed., Academic Press, 1988, vol. 137, pp. 349-366.
Takei K., et al., "Design for a 400-MHz Passive RFID Prototype System for Long Range Applications," to be published in Proc. IEEE Int. Symp. Antennas Propag. 2007.
West, Electrodeposition and Corrosion Processes, 1971.
Wong CM., et al., "Glucose Oxidase: Natural Occurrence, Function, Properties and Industrial Applications," Applied Microbiology and Biotechnology, 2008, vol. 78 (6), pp. 927-938.
Chinese Office Action dated Jun. 14, 2017, regarding CN 201280039622.4.
Chinese Notification of Reexamination dated Apr. 25, 2018, regarding CN 2012800396224.
ELISA Kit Manual Human C3a, catalog #550499, copyright 2001.
ELISA Kit Manual Human C4a, catalog #5550947, revised Feb. 2001.
Heraeus Technical Data Sheet, Thick Film Materials, Product LP11-4493, retrieved from the Internet on Jun. 14, 2019.
Heraeus Technical Data Sheet, Thick Film Materials, Product CL11-5100, retrieved from the Internet on Jun. 14, 2019.
Heraeus Technical Data Sheet, Thick Film Materials, Product CL11-5349, retrieved from the Internet on Jun. 14, 2019.
Heraeus Technical Data Sheet, Thick Film Materials, Product CL11-6109, retrieved from the Internet on Jun. 14, 2019.
Ferro Techinical Data Sheet, 3804 & 4082 Pt Conductors, revised Jan. 2011, retrieved from the Internet on Jun. 14, 2019.
ESL Technical Data Seet, 5542 Print GD and 5542 Pouring GD, retrieved from the Internet on Jun. 14, 2019.
Allcock H.R., et al., "Contemporary Polymer Chemistry," Pearson Education Upper Saddle River, NJ, 2003.
Billmeyer F., Textbook of Polymer Science, 3rd Edition, John Wiley, 1984.
Andrade J.D., Surface and Interfacial Aspects of Biomedical Polymers: vol. 1 Surface Chemistry and Physics, 1985.
Allcock H.R., et al., "Contemporary Polymer Chemistry," Prentice-Hall, 1981.
Standard for ECG Connectors, Association for the Advancement of Medical Instrumentation, May 1983.
Co-pending U.S. Appl. No. 60/269,169, filed Feb. 15, 2001.
Co-pending U.S. Appl. No. 60/423,220, filed Oct. 31, 2002.
Morris C.G., Definition of "Machine Learning", Academic Press Dictionary of Science and Technology (4th ed.), 1992, Oxford, UK: Elsevier Science Technology. Retrieved from https://search.credoreference.com/content/entry/apdst/machine_learning/0?institutionId=743.

* cited by examiner

TISSUE IMPLANTABLE SENSOR WITH HERMETICALLY SEALED HOUSING

CROSS REFERENCE TO RELATED APPLICATION(S)

This application claims the benefit of priority under 35 U.S.C. § 119(e) of U.S. Ser. No. 61/511,930, filed Jul. 26, 2011, the entire contents of which is incorporated herein by reference in its entirety.

GRANT INFORMATION

This invention was made in part with government support under NIH Grant Nos. DK-54545 and DK-77254. The United States government has certain rights in this invention.

BACKGROUND OF THE INVENTION

Field of the Invention

The present invention relates generally to sensors for in vivo detection and measurement of blood solute levels, and more particularly to a hermetically sealed implantable sensor capable of long term monitoring of tissue glucose concentrations by wireless telemetry and methods of use thereof.

Background Information

Diabetes is a major health problem that results in significant mortality, debilitating complications, substantial economic impact on society, and untold waste of human resources. The results of the prospective Diabetes Control and Complications Trial show that complications of diabetes can be significantly reduced by improved blood glucose control. Achieving improved glucose control is problematic for most people with the disease, however, because the most common means for measurement of blood glucose involves blood collection by "finger-sticking," a method that is inconvenient and unacceptable to many people with diabetes, and is rarely performed frequently enough to follow blood glucose dynamics.

Continuous glucose monitoring can now be performed with short term, percutaneous glucose sensors, but this method has certain drawbacks. These sensors utilize a needle introducer to insert a sensing element under the skin, leaving the remainder of the device outside the body. Such systems can remain in place for 3 to 10 days before being replaced. Their performance can be affected by changes that occur in the tissues as a result of the insertion and presence of the implant, which can lead to instability of the glucose signal, and fingerstick glucose assays are needed for regular sensor recalibration during use. Such sensors have therefore not been approved by the Food and Drug Administration as a primary standard for glucose measurement and cannot be fully relied upon to warn the user of an impending hypoglycemic episode.

There are many technical challenges in designing a commercially viable implantable sensor that will meet medical device regulatory and performance requirements, and also be broadly acceptable to users. First and foremost it must be safe, as well as accurate and reliable. To optimize user acceptability for long term application, an implantable sensor should also be compact and be entirely contained within the body, i.e. it should not require any wires or other structures to extend through the skin, which would be unsightly, uncomfortable, and a potential source of infection. Biocompatible materials must be used where portions of the sensor come into physical contact with the body. Fabrication techniques developed in the microelectronics industry along with specialized electrode energization and signal processing techniques offer the potential to solve many of these problems, however, failures and inaccuracies associated with the electrodes and associated structures have been problematic. In particular, there have been problems in designing and mounting the electrodes, and the electrically conductive structures to which they are connected, in a manner that will allow a hermetic seal that prevents signal degradation, shorts, and other failures.

For acceptance by a broad group of users, there is a need for a long term, fully implanted glucose sensor with a wireless telemetry system capable of continuously monitoring glucose levels in a subject, accurately processing the glucose data, and stably transmitting the data outside the body to an external receiver. Such a device and data provided by it could be used in a number of ways to help achieve improved blood glucose control. The device could direct dosing of therapeutics, warn of hypoglycemia, guide diet modification and exercise, or act as an input to an artificial pancreas. It could also be used in conjunction with other forms of therapy such as drugs, transplants, islet replacement or preservation, or stem cells. To be optimally acceptable by users, the sensor should be of a size and shape suitable for comfortable, unobtrusive subcutaneous implantation, should function for at least several months to a year or longer, be implantable by a simple outpatient procedure requiring only local anesthesia, be convenient to use as a data source, be free of significant risk for untoward effects (e.g., be biocompatible and not problematically immunogenic), and not require frequent recalibration.

SUMMARY OF THE INVENTION

The present invention provides implantable sensors for in vivo detection and measurement of analyte levels, and is well suited for monitoring glucose levels. The sensor is well suited to implantation in both solid and gel-like tissues. It permits long term monitoring of glucose levels on a near-continuous or semi-continuous basis by wireless telemetry, and measurements made by the sensor can be insensitive to certain short term and long term changes or variations in the structure or condition of the tissue microvasculature.

The implantable glucose sensor of the present invention includes: a housing having an overall size and shape suitable for comfortable, unobtrusive subcutaneous implantation, which sensor is implantable by a simple outpatient procedure not requiring general anesthesia, convenient to use as a source of data, is free of significant risk for untoward effects (e.g., is biocompatible and is not immunogenic to a problematic extent), and does not require frequent recalibration. The sensor can operate when implanted for at least several months to a year or longer.

Specifically, the sensor includes: a) a biocompatible, hermetically sealed housing having an overall size and shape suitable for comfortable, unobtrusive subcutaneous implantation; b) a detector array comprising at least one detector for detection of an analyte, the at least one detector further including associated membrane layers; c) an electrical power source, such as a battery; d) circuitry operatively connected to the detector array comprising functionality for accurately processing detector signals; and e) a telemetry transmission portal comprising a means for stably conveying processed detector signals to the exterior of the sensor for relay to a receiver outside of a body when the sensor is implanted subcutaneously. In embodiments, certain elements c) and d) are disposed within the interior of the housing, while one or both of b) and e) may be disposed on the housing or disposed such that they join to and effectively form a portion of the housing. In embodiments where the sensor housing material itself may be sufficiently transparent or conductive to the telemetry signals, the telemetry transmission portal may be a portion of the housing, or may comprise the entire housing. In exemplary embodiments, the membrane layers may comprise a source of immobilized enzyme such as glucose oxidase (GO) for catalyzing the reaction of a target analyte (e.g. glucose) and oxygen.

In another aspect, the invention provides a method of monitoring an analyte (e.g. glucose) level in a subject. The method includes: a) implanting a sensor of the present disclosure into a tissue of the subject; b) detecting an analyte level in the subject; and c) wirelessly transmitting sensor signals related to the analyte level via a telemetry transmission portal to an external receiver.

In another aspect, the invention provides a method of monitoring an analyte (e.g. glucose) level in a subject. The method includes: a) implanting a plurality of the sensors of the present disclosure into at least one tissue of the subject; b) detecting sensor signals indicative of an analyte level in the subject; and c) wirelessly transmitting the sensor signals via the telemetry transmission portal to an external receiver.

In another aspect, the invention provides a method of treating diabetes in a subject. The method includes: a) implanting the sensor of the invention into a tissue of the subject; b) continuously monitoring the glucose level in the subject; c) analyzing the glucose level; and d) providing a therapeutic treatment, a therapeutic treatment recommendation, a warning, information to enable certain teaching or training, or combination thereof.

In yet another aspect, the invention provides a method of manufacturing the implantable sensor of the present disclosure. The method includes: a) generating a seal between the housing and a ceramic substrate of the detector array, or between the housing and the telemetry transmission portal via application of a first joining process; and b) generating a seal between at least two portions of the housing via application of a second joining process, wherein the resulting housing is hermetically sealed. In embodiments, the first joining process is performed by generalized heating of a section of the housing and the ceramic substrate or the telemetry transmission portal to produce a seal; and the second joining process is performed by localized heating of the portions of the housing at discrete regions where the seal is generated. In certain embodiments, the first joining process involves the joining of one or both of the ceramic substrate and telemetry transmission portal to flanges, which flanges are then joined to the housing by an additional joining process involving localized heating of portions of the housing at discrete regions in contact with the flange where the seal is generated.

In yet another aspect, the method of manufacturing the implantable sensor of the present disclosure includes: a) generating a seal between a portion of the housing and a ceramic substrate of the detector array; b) installing an electrical connector means into a section of the housing that includes the ceramic substrate; c) establishing electrical connection between the electrodes and the connector means within the housing section; d) connecting external instrumentation to the connector means to test or electroplate the electrodes.

In yet another aspect, an implantable analyte sensor is disclosed. In one embodiment, the implantable analyte sensor includes (i) a biocompatible hermetically sealed housing, (ii) a detector array comprising at least one detector and at least one membrane layer, the at least one membrane layer including at least an enzymatic material, and a membrane structure comprising at least a cavity, the enzymatic material disposed within the cavity, (iii) an electrical power source, (iv) circuitry operatively connected to the detector array, and (v) a telemetry transmission portal.

In one variant, the at least one detector is a plurality of detectors, and the detector array further includes at least one electrolyte layer, at least a portion of the at least one electrolyte layer disposed between the plurality of detectors and the at least one membrane layer. Further, the membrane structure further includes: (i) a bottom wall, (ii) a top wall opposing the bottom wall, (iii) at least one side wall connected to each of the bottom wall and the top wall, the bottom wall, the top wall and the at least one side wall defining the cavity, and (iv) an aperture disposed in the top wall and in communication with the cavity, a non-enzymatic cross-linked protein material disposed within the aperture.

In another variant, the at least one membrane layer includes at least: (i) the enzymatic material, which includes a cross-linked protein material having glucose oxidase and catalase co-immobilized therein, (ii) the membrane structure including at least the cavity and an aperture, the aperture in communication with the cavity, (iii) a non-enzymatic cross-linked protein material disposed within the aperture, the membrane structure and the non-enzymatic cross-linked protein material configured to enclose the enzymatic material within the cavity, and (iv) an electrolyte layer disposed between the at least one detector and the membrane structure.

In yet another variant, the membrane structure further includes an aperture in communication with the cavity, the aperture having a non-enzymatic crosslinked protein material disposed therein, the non-enzymatic cross-linked protein material configured to occlude the aperture and enable diffusion of analyte from the tissues of the body into the cavity for reaction with the enzymatic material when the implantable analyte sensor is implanted subcutaneously.

BRIEF DESCRIPTION OF THE DRAWINGS

As shown in FIG. 1A, the sensor includes housing 2. The top surface of the sensor includes telemetry portal 3, external surface telemetry antenna 4, and anti-migration elements 5 adapted as two fabric velour patches. The sensor of FIG. 1A is 3.4 cm in diameter and 1.5 cm thick.

FIG. 1B shows electronics modules 11, telemetry transmission portal 3, battery 12, conductive battery mounting substrate 13, detector array substrate 14, hermetic braze joint 15, hermetic weld joint 16, detector connection leads 17, antenna connection lead 18, and external surface telemetry antenna 4.

As shown in FIG. 2A, the top surface of the implant includes a telemetry portal 3, which is disposed on a raised surface of the implant housing 2.

As shown in FIG. 3A, the top surface of the implant housing 2 includes a telemetry portal 3.

As shown in FIG. 3C, an end aspect of the sensor includes a telemetry transmission portal 3, through which passes a wire conductor 30, which makes contact with external discrete telemetry antenna 31. Wire conductor 30 and external discrete telemetry antenna 31 are embedded in a radiofrequency-transparent encasement 32 at the end of the sensor housing. The encasement 32 contains suture tie-down holes 33.

DETAILED DESCRIPTION OF THE INVENTION

Figure 1A:
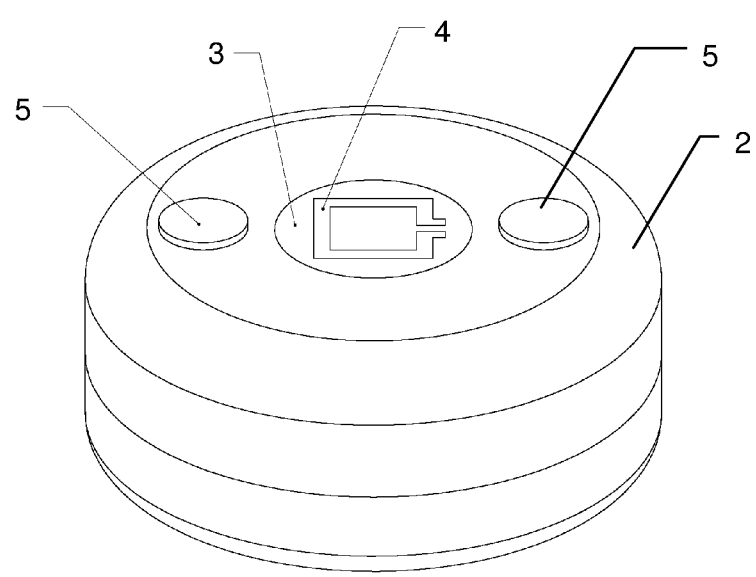
FIG. 1A is a perspective view of a disk-shaped sensor according to an embodiment of the invention.

In one aspect, the present invention provides a tissue-implantable sensor adapted for in vivo detection and monitoring of glucose levels using a detector array communicating with signal processing circuitry and a telemetry transmission portal. The sensor is contained in a fully biocompatible, hermetically sealed housing. The overall size and shape of the housing is well suited to comfortable, safe and unobtrusive implantation in solid and gel-like tissues, especially subcutaneous implantation. The sensor is designed to permit long term monitoring of glucose levels on a near-continuous basis using wireless telemetry to provide a signal outside of the subject's body. Notwithstanding variations in the structure or condition of the tissue microvasculature, the sensor provides clinically accurate signals for monitoring glucose levels.

Before the present compositions and methods are described, it is to be understood that this invention is not limited to the particular device, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the device" or "the method" includes one or more devices and methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, a "sensor" is intended to mean a device including a detector array with at least one detector, as well as other components, such as a housing, electronic circuitry, and a power source, configured and operable to allow generation and processing of signals from electrodes of the detector array. Such signals are utilized to make a determination of glucose concentration in the sensor's biological environment.

As used herein, a "detector" refers to a device that generates, or can be made to generate, a signal indicative of and dependent on the concentration of an analyte, such as glucose or oxygen. Such a device may be based on electrochemical, electrical, optical, mechanical, thermal, or other principles as generally known in the art. Such a device may consist of one or more components, including for example, one, two, or three electrodes, and may further incorporate immobilized enzymes or other biological or physical components, such as membranes, to provide or enhance sensitivity or specificity for the analyte.

As used herein, the term 'biological environment' refers to that volume of biological material in communication with a sensor, whose concentration of an analyte, such as glucose, is capable of being measured by the sensor. Typically, the volume of biological material is in the immediate vicinity of a detector array, or single detector thereof.

The sensor of the present invention generally includes: a) a biocompatible, hermetically sealed housing having an overall size and shape suitable for comfortable, safe and unobtrusive subcutaneous implantation; b) a detector array comprising at least one detector, the at least one detector further including associated membrane layers, wherein the membrane layers comprise a source of immobilized enzyme such as glucose oxidase (GO) for catalyzing the reaction of a target analyte (e.g. glucose) and oxygen; c) an electrical power source; d) circuitry operatively connected to the detector array comprising functionality for processing detector signals; and e) a telemetry transmission portal comprising a means for stably transmitting processed detector signals to the exterior of the sensor for relay to a receiver outside of a body when the sensor is implanted subcutaneously. Certain elements c) and d) are disposed within the housing, while b) and e) may be disposed within or upon the housing. In various embodiments, the sensor may further include one or more electronics modules optionally accommodating the circuitry and functionality for accurate processing of signals indicative of analyte levels in the subject, as well as other functionality as discussed further herein.

Figure 1B:
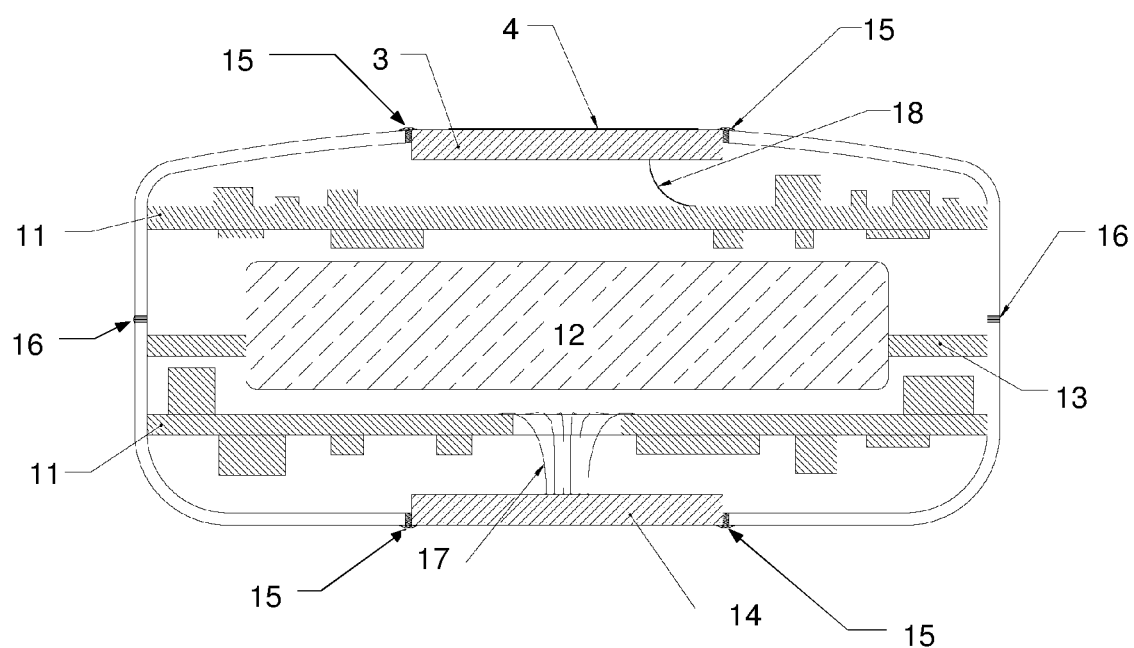
FIG. 1B is a cross-sectional view of the sensor of FIG. 1A.
Figure 2A:
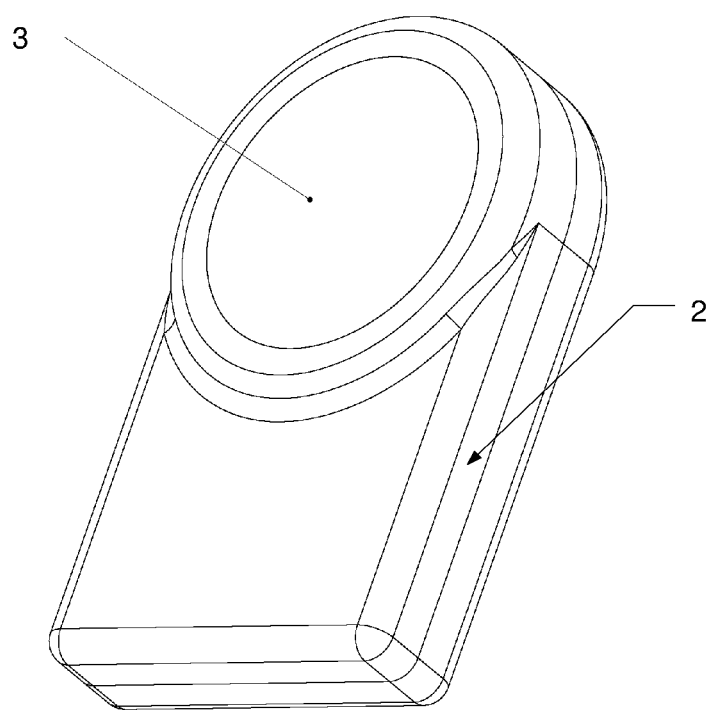
FIG. 2A is a perspective view of an elongate-form, variable-thickness sensor according to an embodiment of the invention.
Figure 2B:
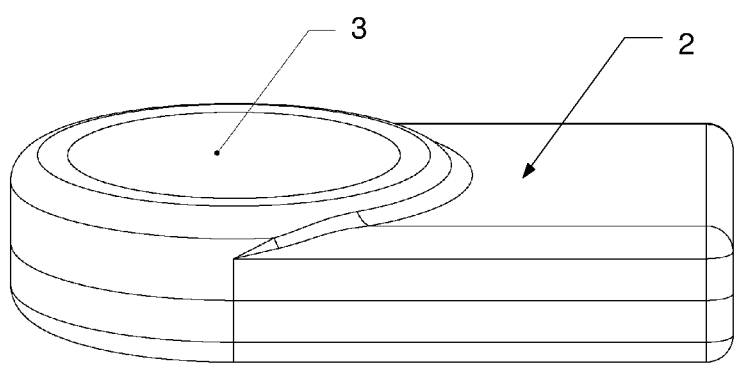
FIG. 2B is a side-facing perspective view of the sensor of FIG. 2A.

FIG. 1A is a perspective view of a sensor according to one embodiment of the invention. FIG. 1B is a cross-sectional view of the sensor of FIG. 1A and depicts the general schematic of the sensor. The sensor of FIG. 1B includes electronic modules 11, a telemetry transmission portal 3, an electrical power source, e.g., a battery 12, conductive battery mounting substrate 13, detector array substrate 14, hermetic braze joint 15, and hermetic weld joint 16.

As depicted, for example in FIG. 1B, the sensor may include one or more electronics modules. FIG. 1B depicts an embodiment in which two electronics modules are provided. However, it is envisioned that any number of modules may be incorporated into the device so long as the device remains of a suitable compact size for prolonged biological implantation. For example, 1, 2, 3, 4, 5, 6, 7, 8, 9, 10 or more modules may be incorporated depending on the desired functionality. Further, the modules may be arranged in a variety of configurations depending on the overall layout of the sensor as well as the shape of the housing accommodating the components.

Typically the electronics modules are configured to accommodate the circuitry and accurate signal processing functionality in communication with the detector array such as the intermediate detector connection module. By "accurate signal processing" is meant that one or more electrical signals are received and correlated to a level of analyte in the subject's body to a clinically useful degree (e.g., with glucose as the analyte, to permit medical or dietary management of a glucose concentration-related condition, such as diabetes). Preferably, such signal processing is provided with minimal delay (lag) in readings. As illustration, the Examples provide data from animal testing of a sensor according to the invention in which the average value of the rising delay measured was 11.8±5.7 min (mean±SD) and of the falling delay was 6.5±13.3 min, based on 34 intravenous glucose tolerance tests in a subject during a nondiabetic period. Of these values, 2.5±1.2 min was ascribable to the sensor itself, as determined from independent in vitro measurements, and an estimated 0.5 min was ascribable to circulatory transport from the central venous infusion site to the implant site. The remainder of the rising and falling average delays (8.8 and 3.5 min, respectively) was attributable to mass transfer and physiologic phenomena within the local tissues. Over the extended implant period, there was no significant systematic change in either average delay value. Variations in delay values from approximately 4 to 12 min in humans are acceptable in this context, and results with the sensor of the present disclosure compare favorably to a retrospective correlation between sensor signals and finger-stick assay values estimated a statistical delay of approximately 10 minutes.

The electronics modules may also include components to effectuate functionality for a number of additional analyses and operations. By way of illustration, functionality may be provided for data storage and memory, analysis of analyte levels, telemetry, encryption, and the like. For example, the modules may include means for processing and calibrating signals, adjusting signals and estimating analyte concentrations. Such means and functionality are described in Gough, U.S. Pat. No. 7,248,912, incorporated herein by reference in its entirety. Certain of such functionality may alternatively be provided by additional signal processing means in the external receiver, which arrangement can help to minimize power consumption in the implanted device and maximize the implanted device's battery lifetime.

The telemetry transmission portal (which may be provided as a plurality of portals disposed on multiple sides of the housing) allows for wireless transmission of signals outside of the subject's body to an external receiver via an antenna. In some embodiments, the telemetry system samples the electrical currents from individual detectors of the detector array, encodes the samples into multiplexed signal segments, and transmits the segments as a train of radio-frequency signals at regular intervals to an external receiver, where the signals are decoded and recorded. Radio-telemetry may be accomplished at a variety of predetermined frequencies. An exemplary range of telemetry carrier frequencies is from about 30 MHz to about 3000 MHz. Within this broader range, additional exemplary ranges include from about 314 MHz to about 316 MHz, from about 401 MHz to about 406 MHz, from about 433 MHz to about 435 MHz, from about 863 MHz to about 870 MHz, from about 902 MHz to about 928 MHz, and from about 2360 MHz to about 2500 MHz.

The portal may be electronically coupled to the detector array or individual detectors thereof via potentiostat and telemetry transmitter circuitry. In embodiments, the portal may be electronically coupled to the detector array or individual detectors thereof via one or more electronics modules. The portal is preferably integrated into the housing and the housing hermetically sealed, as further described herein.

In some embodiments, the portal may comprise an electrical path such as a wire, leading from the interior of the housing to the exterior of the housing, so as to convey telemetry signals generated inside the sensor to the exterior of the sensor. In such embodiments, such electrical path leads outside the sensor to a transmitting antenna, which may be disposed on the surface of the portal, or on or within an aspect of the housing, or which may extend from the housing.

In some embodiments, the telemetry portal comprises a transformer coupling or capacitive coupling element, and the portal is further sealed hermetically into the housing. In such embodiments, telemetry signals produced in the interior of the sensor are conducted to the outside of the sensor by means of such coupling element, and once provided outside the sensor are available for further radiation and detection by an external receiver.

In some embodiments, the telemetry portal comprises a radiofrequency-transparent or semi-transparent window, which is nonetheless sealed hermetically into the housing. In such embodiments, a telemetry transmitting antenna is provided inside the sensor, and telemetry signals produced from such an antenna are thus radiated through the portal to the outside of the sensor and thus radiated outside the body and available for detection by an external receiver.

In some embodiments, the telemetry portal itself comprises an antenna, when, for example, conductive structures embedded within the portal provide means for radiating telemetry signals outside the body. In such embodiments, the portal is hermetically sealed into the housing, and telemetry signals produced in the interior of the sensor are radiated by the portal outside the sensor, and once radiated outside the sensor are available for further radiation and detection by an external receiver.

In some embodiments, where the sensor housing material itself may be sufficiently transparent or conductive to the telemetry signals, a portion of the sensor housing (or in some embodiments the entire housing) may be employed to serve as the telemetry transmission portal. In such embodiments, a telemetry transmitting antenna or other radiating or coupling element is provided inside the sensor, and telemetry signals produced from such antenna or coupling element are thus radiated to the outside of the sensor through the housing and thus radiated outside the body and available for detection by an external receiver.

In some embodiments, the transmission of signals to an external receiver may be maximized by implanting the sensor in a particular orientation dependent on the location of the telemetry transmission portal within the sensor housing. Implantation of the sensor such that the telemetry transmission portal is oriented toward or facing the skin, or is not otherwise shielded from the skin by an aspect of the sensor housing, maximizes signal strength since the signal is required to travel through minimal intervening sensor components and biological tissue before being received by an external device. Thus in one embodiment, the telemetry transmission portal is disposed on, within, or near a wall of the housing that is implanted in tissue facing toward the dermis of the subject's skin.

The detector array of the present invention typically includes a plurality of individual detectors disposed on a common platform, and that function as a group. The total number of detectors on a sensor is limited only by the surface area of the detector disc, which in turn is dictated by a desire to minimize the overall size of the sensor. In all embodiments of the sensor, use of a multiplicity of detectors: 1) maximizes the probability that several detectors will be positioned very near an active vascular bed; 2) affords the possibility of ignoring a given detector if it is or becomes erratic or nonresponsive over time; and 3) minimizes the effects of local variations in analyte concentration, as well as local variations in the magnitude of any potentially confounding phenomena. In various embodiments, the detector array includes at least one detector, but may include up to 2, 3, 4, 5, 6, 7, 8, 9, 10, 11, 12, 13, 14, 15, 16, 17, 18 or more detectors. Typically, each detector includes a working electrode in operative contact with a counter electrode and a reference electrode, as well as associated membrane layers.

Typically, working and counter electrodes are commonly fabricated from the platinum-family noble metals, because of such metals' catalytic properties and resistance to corrosion. Such metals include ruthenium, platinum, palladium, rhodium, iridium and osmium. In an exemplary embodiment, such as shown in the sensor of Example 1, platinum is used. Reference electrodes are commonly fabricated from silver/silver chloride (Ag/AgCl), but other materials that form electrochemical couples with suitably high exchange current densities may be utilized. Alternative electrode materials include gold as well as other metals generally known in the art.

The detector array substrate 14 preferably comprises a ceramic material, as described below, and metallic base structures for the working, counter, and reference electrodes are preferably deposited onto the substrate by techniques known in the art including but not limited to sputtering, chemical vapor deposition, evaporation ("thin film" techniques), and screen printing (a "thick film" technique). Connections to the electrodes as are required during operation of the sensor for energization and signal measurement, or for use during manufacturing, are preferably made via feedthroughs 55 that may extend through the detector array substrate to the interior of the sensor. Additional metals and required electrode layers (such as platinization, silver, and silver chloride) may be deposited onto such base structures by techniques known in the art including but not limited to electroplating. When electroplating is utilized, a convenient means to make the necessary electrical connections to the electrodes is provided by electrical connector 23, which contains contacts to the electrodes. Electrical connector 23 also provides a convenient means to accomplish tests and in-process checks as may be useful during manufacture of the device, before the device is fully assembled, and also provides convenient means to connect electronics modules within the sensor to the electrodes, as is required to enable function of the sensor.

Those of ordinary skill in the art will appreciate that alternatives to the particular sensor and detector dimensions, construction and geometry as described and shown in the figures will be suitable for implantation use according to the invention, so long as the basic configuration of detectors is utilized, and the signal processing functionality of the invention are employed. Such sensors may be adapted for qualitative and quantitative detection and measurement of any number of different analytes and solutes, in addition to those specifically exemplified herein.

As discussed above, the detector array of the present invention typically include a plurality of detectors disposed on a common platform. In various embodiments, the platform may be a ceramic, such as a generally planar ceramic substrate. Ceramic substrates may be formed via sintering of green ceramic bodies which may include a powdered inorganic component comprising oxides, carbides, borides, nitrides, and silicides of aluminum, zirconium, beryllium, silicon, titanium, yttrium, hafnium, magnesium and zinc combined with an organic binder and optionally other organic compounds. Volume ratios of inorganic to organic binder may range from 50:50 to 100:0, such as a range of 70:30 to 95:5, or 80:20, or 90:10. The ceramic substrate should be of any thickness appropriate to meet the mechanical strength and hermeticity requirements of a long term implantable device while remaining sufficiently thin so as to enable construction of a compact device. As such, the ceramic body may have a minimum thickness of at least 0.02, 0.03, 0.04, 0.05, 0.06, 0.07, 0.08 inches or greater. For example, in one embodiment, the ceramic body is composed of alumina and has a thickness of between about 0.04 to about 0.08 inches.

As will be appreciated by those of skill in the art, ceramic bodies may be formed in any number of planar or non-planar geometric shapes. In some embodiments, a ceramic body for use in the present invention may be virtually any geometric shape depending on the desired array design, such as, for example, round, oval, elliptical, rectangular, triangular, star shaped, square and the like, although round bodies are generally preferred because such shapes are more amenable to typical hermetic joining operations such as brazing.

In embodiments where glucose is the analyte to be measured (using oxygen or hydrogen peroxide detection), the detectors are preferably of the enzyme-electrode type, employing membranes containing immobilized glucose oxidase. Those of ordinary skill in the art will be familiar with the fundamentals of glucose detector construction, so the materials, methods and alternative forms of construction for such detectors need not be repeated here. By way of example, the following disclosures are incorporated herein by this reference in their entireties as reflecting non-essential but representative information concerning standard construction techniques for glucose detectors and sensors: Gough, U.S. Pat. Nos. 4,484,987; 4,671,288; 4,650,547 and 4,890,620; in Allen, U.S. Pat. No. 5,322,063; in Schulman, U.S. Pat. No. 5,660,163; and in Gough, U.S. Patent Publication No. 20020156355.

Methods for calculating the levels of glucose present as a substrate of a specific enzymatic reaction are well known in the art, as are certain calibration techniques (see, e.g., Choleau, et al., *Biosens. Bioelectron.*, 17:647-654 (2002) and Choleau, et al., *Biosens. Bioelectron.*, 17:641-646 (2002), the teachings of which are incorporated herein by reference). Benchmark data for evaluation of sensor performance are also available (Bremer, et al, *Diabetes Technol. Ther.*, 3:409-418 (2001), the teachings of which are incorporated herein by reference).

The detector array for detection of glucose in an embodiment is based on the following two-step chemical reaction catalyzed by glucose oxidase and (optionally) catalase as described in Armour et al. (*Diabetes* 39, 1519-1526 (1990)):

$$glucose + O_2 \rightarrow gluconic\ acid + H_2O_2$$

$$H_2O_2 \rightarrow \tfrac{1}{2}O_2 + H_2O$$

resulting in the overall enzyme reaction (when catalase is present):

$$glucose + \tfrac{1}{2}O_2 \rightarrow gluconic\ acid$$

The two enzymes are immobilized within a gel matrix that is preferably crosslinked for mechanical and chemical stability, and that is in operative contact with a working electrode of a detector that electrochemically senses oxygen. Glucose and ambient oxygen diffuse into the gel and encounter the enzymes, the above reactions occur, and oxygen that is not consumed in the process is detected by the electrode. Note that intervening membrane layers may be included to protect the electrode from drift in sensitivity due to contact with certain non-oxygen chemical species (e.g. electrode "poisoning"), but the detector will nonetheless be arranged sufficiently close to the enzyme gel to enable detection of oxygen levels therein. In embodiments based on "oxygen-sensing differential measurement," after comparison with the background oxygen concentration detected by a separate oxygen reference detector, the difference is related to glucose concentration. The sensor in such embodiments is therefore minimally composed of (i) a main or primary detector for detecting glucose, which comprises an oxygen-detecting electrode with an immobilized enzyme gel that produces a glucose-modulated, oxygen-dependent current ($i_{gmo}$); (ii) a reference or secondary detector that detects oxygen without enzymes that produces an oxygen-dependent current ($i_o$); and (iii) a signal-processing element that takes the difference of (i) and (ii) to give the signal of interest—the glucose-dependent difference current ($i_g$).

In such embodiments that incorporate an oxygen-sensing differential measurement configuration, it is an optional object of the invention to tailor the design of the membranes of the main and reference detectors such that the response times of each detector to a change in oxygen level are made to closely match. By such matching of response times, artifactual fluctuations in the sensor-reported glucose level (otherwise owing to mismatch of detector oxygen response times) may be minimized.

The detector may be calibrated before, after, and during implantation, and preferably needs infrequent recalibration (no more than one time per day, preferably no more than one time per week, most preferably no more than once every 10 days or longer). To that end, calibration may be performed with the formula $BG = k_1 i_o F(k_2 i_g / i_o)$, where BG is blood glucose, $k_1$ is the oxygen mass transfer coefficient for the reference detector, $k_2$ is the glucose mass transfer coefficient related to the implant environment, and F is a monotonic sensitivity function of the glucose sensor determined in vitro or in vivo, which may be quasi-linear, piecewise-linear, or of other defined form such as exponential. With an appropriately designed immobilized enzyme gel structure, such as that described in U.S. Pat. No. 7,336,984, which is incorporated herein by reference in its entirety, the sensor can remain responsive to glucose in the tissue implant environment over clinically relevant concentration ranges. This calibration relation is an adaptation of methods as described in Gough et al. (*Anal. Chem.* 57, 2351-2357 (1985)) and U.S. Pat. No. 7,336,984.

As an alternative to the oxygen-sensing differential measurement configuration, glucose detectors can be constructed to respond to the reaction product hydrogen peroxide. The signal of interest is then the direct detector output. The invention can be applied to either configuration, or to other arrays of chemical detectors designed for implantation.

In embodiments, main detectors may be provided with different sensitivities to glucose/oxygen ratios, in order to maximize the sensor's overall range of responsiveness. For example, certain main or primary detectors may be included with heightened sensitivity at low values of glucose-to-oxygen ratio for enhanced transduction fidelity at low glucose or high oxygen levels, whereas other main or primary detectors may be provided with enhanced range to avoid "saturation" (i.e. loss of signal) at high values of glucose-to-oxygen ratio.

In some embodiments of the invention, the detector array includes primary detectors responsive to the analyte, such as glucose, and other secondary detectors responsive to potentially confounding phenomena. In a manner that is dependent on the particular analyte and the detector technology, the sensor signals may be combined to produce a measure of the analyte concentration.

Use of several different measurement paradigms, collectively or individually, is made possible by the presence of multiple detectors within the sensor. For example, in a glucose sensor, the use of a multiplicity of detectors allows one to combine signals from all detectors to provide a weighted average glucose value. Measurements used to obtain the average value may be taken temporally, i.e., at different points in time, or simultaneously. Values may also be taken spatially, e.g., from detectors at different positions on the detector platform. The effect of variations in performance by individual detectors at any given time may therefore be minimized.

In some embodiments of the invention, analyte concentrations are calculated corresponding to each primary detector and subsequently weighted and summed, i.e., a weighted average value is calculated using only signals from those detectors providing a predetermined minimal signal, indicative of proximity to a vascular source. To this end, the most active detectors are identified, using either an extrinsic stimulus, such as an administered glucose challenge, or using only the signals from the detectors, and then, only the signals of the most active detectors are used for analyte concentration measurement.

In embodiments, the algorithms required to conduct the various paradigms, such as analyte measurement, interpretation of confounding phenomena, the process for identification of minimally active detectors, and the like, may be incorporated into the functionality of the internal electronics modules or other internal circuitry, or alternatively, into external electronic circuitry which is activated after the signals from individual detectors are conveyed to an external receiver.

Materials utilized in the sensor must be inert, that is they may not release substances that would significantly interfere with the detector operation, and moreover, for implantable sensors, the materials must be biocompatible. Again, those of ordinary skill in the art will be readily familiar with suitable material choices for use in the various elements of the invention such as, for example, the biocompatible, implant-grade alumina utilized in the construction of the detector array of Example 1, or other biocompatible metals (e.g., cobalt-chrome alloys or titanium), other ceramics, or mixtures thereof. As further described herein, use of certain coatings can enhance the biocompatibility and/or non-immunogenicity of a material for use in the sensor, which material may not itself be fully biocompatible and/or fully non-immunogenic.

Figure 5A:
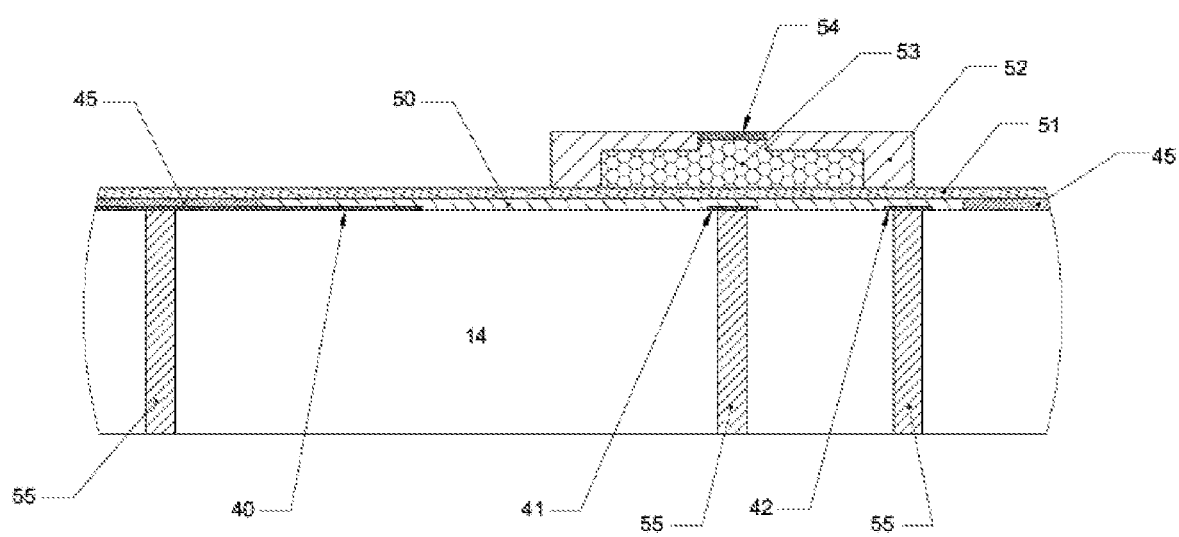
FIG. 5A is a cross-section view of a single detector of a detector array of a sensor according to an embodiment of the invention. In this embodiment the detector is shown including membrane layers. Shown are: counter electrode 40; working electrode 41; reference electrode 42; insulating detector array substrate 14; insulating material 45; electrolyte layer 50; inner membrane 51; membrane shell 52; membrane body 53; and coating membrane layer 54. Electrical connection to the electrodes is made by means of feedthrough pins 55.

As shown in FIG. 5A, the sensors of the present invention may include a variety of different membranes or membrane layers. Such membranes or membrane layers are associated primarily with the structure of the individual detectors of the detector array, although certain membrane layers may be disposed in a continuous fashion across the entire detector array surface or portions thereof that include multiple detectors. FIG. 5A is a cross-section of an individual detector of a detector array in an embodiment. Membrane body 53 includes enzymes immobilized within a gel matrix that is in operative contact with working electrode 40 through the interposed inner membrane 51 and electrolyte layer 50 to allow electrochemical sensing of oxygen. In the embodiment, inner membrane 51 is continuous across the array surface and is therefore a single common layer utilized by all detectors in the array.

Typically, the crosslinked gel of the membrane body 53 is a hydrophilic material. The hydrophilic material of the membrane is permeable to both a large molecule component such as glucose and a small molecule component, such as oxygen, in the solution and is disposed to provide a path through the membrane from the body of solution being assayed.

As noted above, an enzyme or a catalyst for promoting the reaction between the large and small molecule components is immobilized in the hydrophilic material of membrane body 53 for action on these components as they diffuse through it. In various embodiments, materials useful for preparing membrane body 53, i.e., the immobilized enzyme layer, include, in addition to an enzyme component, polyacrylamide gels, glutaraldehyde-crosslinked collagen or albumin, polyhydroxyethylmethacrylate and its derivatives and other hydrophilic polymers and copolymers, in combination with the desired enzyme or enzymes. The layer can similarly be constructed by crosslinking glucose oxidase or other enzymes with chemical crosslinking reagents, without incorporating additional polymers.

In embodiments, the electrochemical detectors are further provided with additional membrane layers made of a hydrophilic electrolyte material (for a bottom first layer) and a hydrophobic material (for a second layer). As shown in FIG. 5A, electrolyte layer 50 is a layer including the hydrophilic electrolyte material which is in direct contact with working electrode 41, reference electrode 42 and counter electrode 40. In various embodiments, suitable materials for constructing the hydrophilic electrolyte layer 50 include salt-containing polyacrylamide gels, glutaraldehyde-crosslinked collagen or albumin, polyhydroxyethylmethacrylate and its derivatives, and other hydrophilic polymers and copolymers, in both crosslinked and non-crosslinked form. The hydrophilic electrolyte layer can alternatively be constructed by providing a mechanical recess or well 44 to contain a liquid electrolyte salt solution or flowable or non-flowable hydrophilic polymer gel, (e.g. as shown in FIGS. 4A-4D).

It is preferred that the width and thickness of the well 44 be selected to be within certain ranges, so as to ensure that minimum electrical conductivity requirements are met and also so that diffusion paths are not caused to be excessively long, leading to delays in detector response. It is desirable that the thickness of the well be within a range from about 5 microns to about 200 microns, or more particularly from about 10 microns to about 75 microns. It is desirable that the width of the well be within a range from about one-half the working electrode diameter (or diameter equivalent) to about 10 times the working electrode diameter, or more particularly from about the working electrode diameter to about four times the working electrode diameter.

Hydrophobic material is provided as inner membrane 51 which is disposed over the electrolyte layer 50 and alternatively over portions of the membrane body 53 as discussed in more detail below. Such material is impermeable to the larger or less soluble molecule component but permeable to the smaller or more soluble molecule. The hydrophobic material limits the surface area of hydrophilic material exposed for accepting large molecule components from the solution and thus reduces the rate of entry of such components to a value which is a function of the concentration existing in the solution, so that the rate of component entering is that which would enter from a more dilute solution in the absence of the hydrophobic material. Additionally, substantial surface area of hydrophobic material is provided for accepting the small molecule component. Alternatively (not shown), the hydrophobic component may be dispersed as small domains in a continuous phase of the hydrophilic material to reduce the front along which the large molecule component can be transported and so reduce its effective diffusion coefficient or transport rate, while the small molecule material can diffuse at a high rate since it can move through both the hydrophilic material and hydrophobic domains. The result of limitation of the rate of entry and/or transport of the larger molecule component and the increased rate of entry and transport of the smaller molecule increases the ratio of small molecule material to large molecule material passing into the membrane body, compared to that which would otherwise exist in the absence of such limitation.

In various embodiments, materials useful for preparing hydrophobic layers, including inner membrane 51 as well as membrane shell 52, include organosilicon polymers, such as polydimethylsiloxane (PDMS) and derivatives thereof, polymers of tetrafluoroethylene or its fluorochloro analogs alone or as copolymers with ethylene or propylene, polyethylene, polypropylene, cellulose acetate, and other oxygen-permeable polymeric materials. For embodiments where the detectors are intended to be responsive to hydrogen peroxide or other such substrate, the hydrophobic layer 51 must be permeable to such substrate, and may necessarily possess some hydrophilic characteristics. In certain embodiments, inner membrane 51 and membrane shell 52 are coextensive and disposed as one membrane layer in which membrane shell 52 and inner membrane 51 are of the same height thereby forming a uniform thickness of membrane across the individual detector and array. However, as shown in FIG. 5A, membrane shell 52 and membrane body 53 may be disposed as regions that create three-dimensional structures on the detector by creating spaced-apart regions of increased thickness as discussed below, although inner membrane 51 in such cases may be disposed across sections of the detector array in a continuous fashion, such that multiple detectors make common use thereof.

Generally, the thickness of each of the membranes disclosed herein is not particularly limited, as long as desired permeability properties are achieved. However, particular requirements for sensor time response characteristics may limit the allowable membrane thickness, since thicker membranes will extend the times required to reach a new diffusional steady-state during substrate concentration transients. Membrane thickness can be, for example, about 1 micron to about 1000 microns, or more particularly, about 10 microns to about 500 microns, or more particularly about 25 microns to about 250 microns, or more particularly about 25 microns to about 75 microns. Very thin membrane layers, particularly those less than about 10 microns, may require mechanical support to be provided in the form of a backing membrane, which may be a porous, relatively inert structure.

Figure 3A:
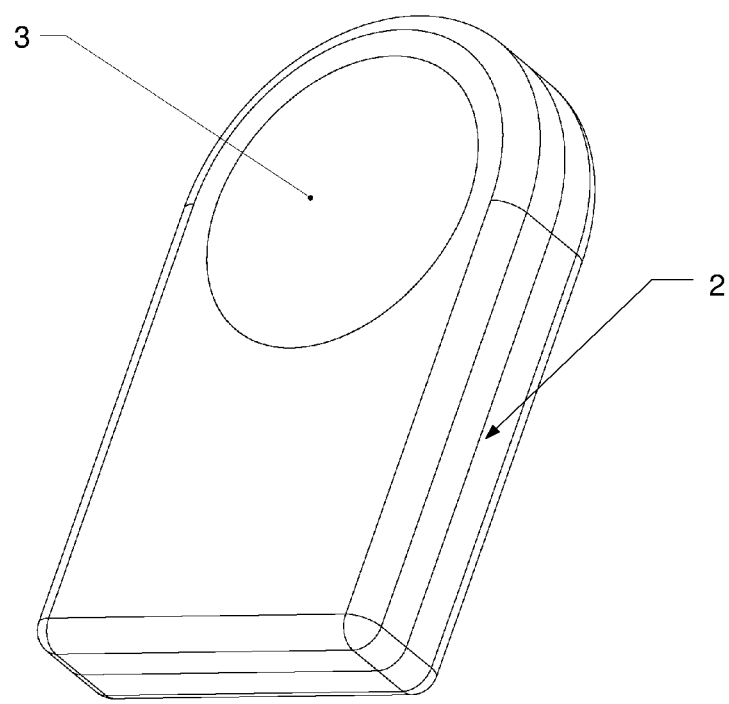
FIG. 3A is a perspective view of an elongate-form, uniform-thickness sensor according to an embodiment of the invention.
Figure 3B:
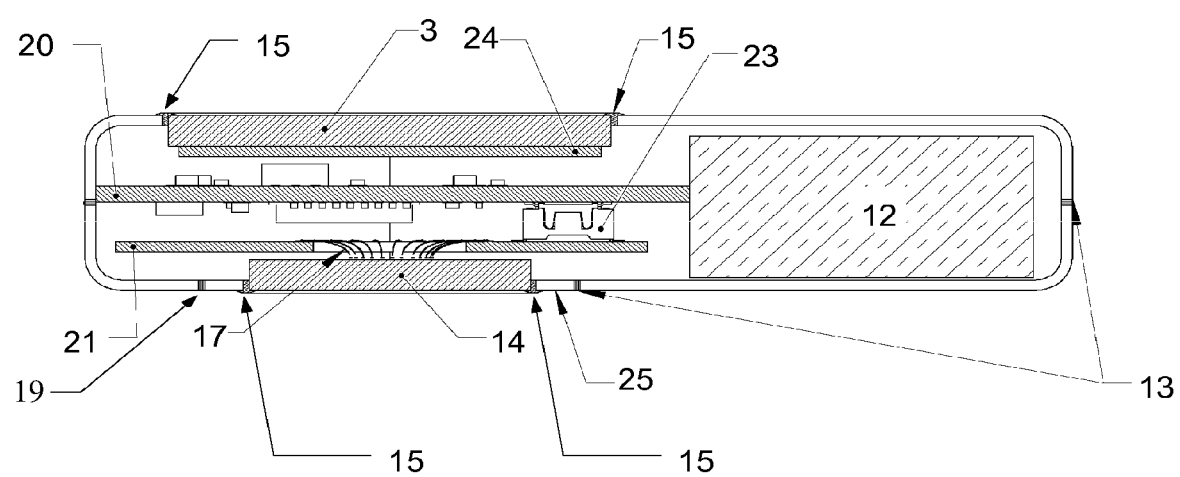
FIG. 3B is a cross-section view of the sensor of FIG. 3A. The cross-sectional schematic view shows two-sided electronics module 20, telemetry transmission portal 3, battery 12, detector array substrate 14, intermediate detector connection module 21, detector connection leads 17, electrical connector 23, internal telemetry antenna 24, hermetic braze joint 15, housing flange piece 25, and hermetic welds 19.
Figure 3C:
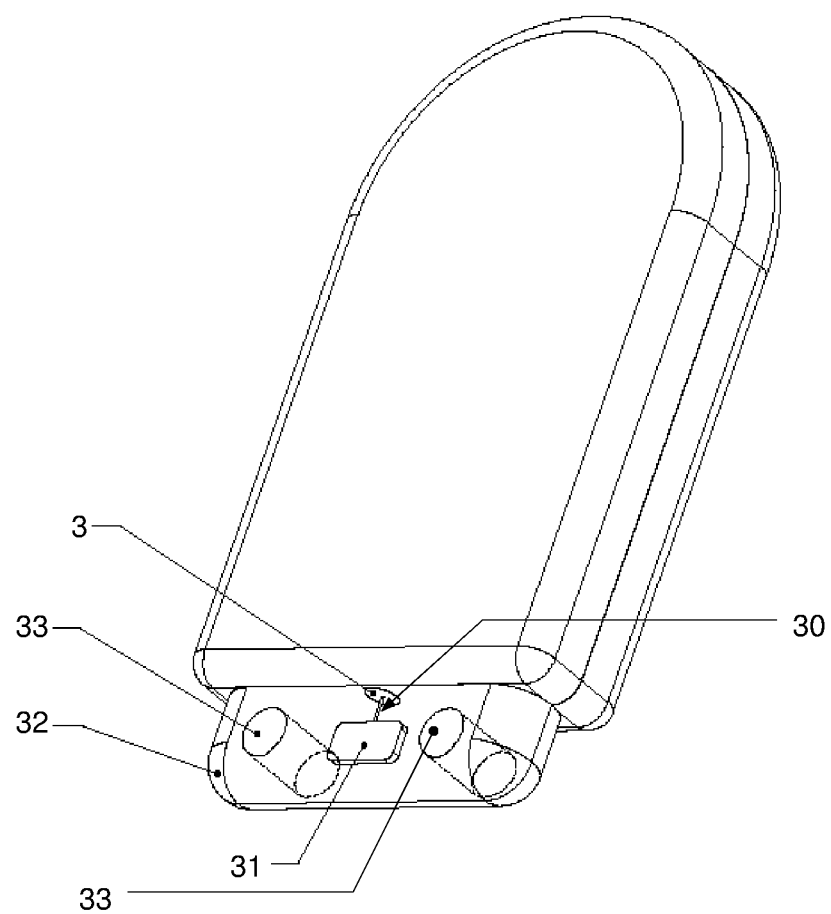
FIG. 3C is a perspective view of an elongate-form sensor according to an embodiment of the invention.

Of significant importance to achieving stability of location of an implanted device is the prevention of migration of the device away from its original implant location in the tissue. To prevent such movement or migration, tissue anti-migration elements may be utilized in various embodiments of the sensor. Tissue anti-migration elements may prevent movement of the device within the implanted tissue by promoting ingrowth of tissues into such elements, such as connective tissue, which can assist in adhering the sensor to the surrounding tissue space. As such, tissue anti-migration elements as used herein may be elements disposed on the sensor that allow connective tissue or other tissue attachment or ingrowth. In one embodiment, a tissue anti-migration element may include a biocompatible mesh, fabric or three-dimensional structure disposed on a surface of the sensor, and it may include polymeric, metallic, or ceramic materials. For example, FIG. 1A shows a device having two fabric velour patches to promote ingrowth of cells. In another embodiment, a tissue anti-migration element may include a feature on the sensor intended to facilitate the attachment of the sensor to the tissue by means of a suture, to be placed at the time of implantation. An example of such a feature is shown in FIG. 3C as holes 33 in an otherwise solid encasement 32 which is located at an end of the sensor. As known in the art, other structures for engagement with a suture, such as a wire loop or loops that are permanently welded or affixed to the sensor housing may also be utilized. Tissue anti-migration elements may also include agents for enhancing or promoting cellular attachment as well as ingrowth, such as cell adhesion molecules, e.g., fibronectin and laminin, as well as anti-thrombotic and/or anti-platelet agents, such as heparin.

Creating a membrane with specific geometric properties can minimize or eliminate the potential for movement of the tissue surface relative to the detectors and thereby improve overall signal fidelity. In embodiments, tissue anti-slip elements are provided as three-dimensional structures defined by membranes of the sensor. For example, a sensor of the present invention having a planar detection array may include a multi-part membrane layer structure as shown in FIG. 5A. For example, FIG. 5A shows a three-dimensional structure disposed over the working electrode 41 via the membrane body 53 and membrane shell 52.

Although basic function can be realized using a layered membrane structure that is uniformly thick over the entire planar array, such that the outer surface of the hydrophobic layer 51 and hydrophilic component 50 of the layers are at a uniform height across the array, it is an object of the present invention to vary the thickness of one or more membranes in a specific fashion to help ensure that tissue contact is maintained when the sensor is implanted in a tissue environment. Each detector region, may, therefore, be constructed with a membrane wherein a portion of the membrane protrudes above the detector array surface to encourage reduced slippage or "locking" of the membrane into the tissue. Aspect ratios for such three-dimensional protruding features may range from about one unit tall for every one unit wide, to about one unit tall for every 5, 10, 20, or 40 units wide. Such tissue anti-slip elements are provided by the structure of this membrane system thereby allowing tissue to locate between the individual membrane structures, thereby mechanically preventing significant rotation or slippage of the tissue-membrane interface. The three-dimensional geometry also increases the surface area of the membrane in contact with the tissue and allows for greater analyte flux to the detection region, e.g., the working electrode, thus providing a higher signal to noise ratio.

Figure 5B:
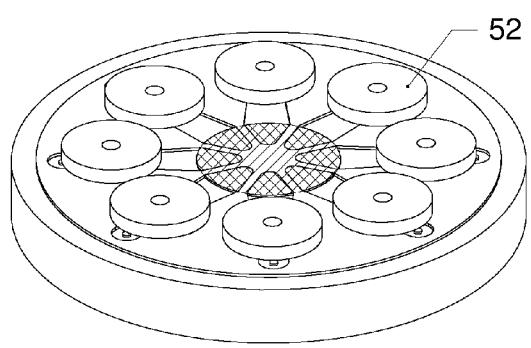
FIG. 5B is a perspective view of a detector array according to an embodiment of the invention including multiple detectors of the type depicted in FIG. 5A. The array includes eight separate detector channels. In this embodiment, membrane shells 52 having a circular shape are shown disposed on each of the detectors.
Figure 5C:
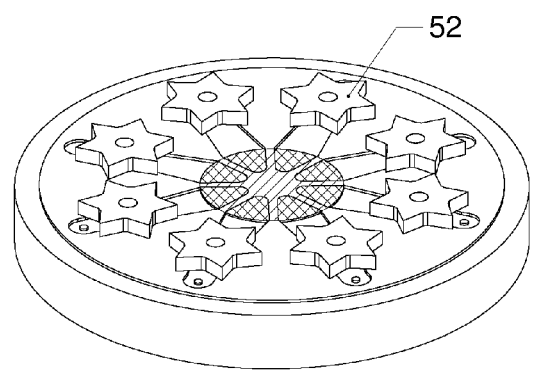
FIG. 5C is a perspective view of a detector array according to an embodiment of the invention. The array includes eight separate detector channels. In this embodiment, membrane shells 52 having a non-circular shape are shown on each of the detectors.

As will be appreciated by one skilled in the art, the three-dimensional tissue anti-slip structures of the membrane may be formed in any number of geometric shapes. For example, FIG. 5B depicts a detector array having individual detectors disposed in a radial configuration. Above each working electrode is provided a circular tissue anti-slip element formed by the membrane shell 52. FIG. 5C depicts star-shaped anti-slip elements formed by membrane shells 52. As such, in various embodiments, the structures may be round, oval, elliptical, star shaped, rectangular, triangular, square, hexagon, octagon, or any other geometric shape. Additionally, the upper surface of the structures need not be flat, as is depicted in FIGS. 5A, 5B, and 5C. Rather, such upper surfaces may be curved, or may include projections of various geometric shapes, or such surfaces may be textured.

As discussed herein, the sensor is biocompatible to allow for long term implantation into biological tissue. Thus all membrane structures that are in direct contact with the surrounding biological material must be biocompatible and not problematically immunogenic. The membrane materials disclosed herein that are in direct contact to tissue are generally known to be biocompatible and suitable for long term implantation. However, in embodiments, all or discrete regions of the sensor may include one or more additional coating membrane layers of non-erodable biocompatible material, which may be included to ensure that the immunogenic potential of all exposed materials remains suitably low. The membrane layer 54 in FIG. 5A is provided as an example of a coating membrane layer that could be employed if the immunogenic potential of the membrane body 53 in an embodiment is not otherwise sufficiently low. Such a coating membrane, by preventing direct contact with the tissue by such membrane body material, allows use of an otherwise immunogenic membrane body material while avoiding any immune response by the tissue. As will be apparent to those skilled in the art, coating membrane layer 54 could be provided and affixed to the sensor as a separate material layer in operative contact with membrane body 53, or it could be intimately joined to membrane body 53 across the area of contact, or it could be formed-in-place by chemical or other treatments of the upper surface of membrane body 53, including various de-immunizing treatments. In all cases, it is required that coating membrane layer 54 be sufficiently permeable to analytes and co-reactants as are intended to permeate membrane body 53 to enable correct operation of the detector.

For example, an outer membrane of a crosslinked collagen or albumin may be utilized. Additionally, other biostable polymers suitable as coating membranes include, for example, polyurethanes, silicones, poly(meth)acrylates, polyesters, polyalkyl oxides (polyethylene oxide), polyvinyl alcohols, polyethylene glycols and polyvinyl pyrrolidone, as well as hydrogels such as those formed from crosslinked polyvinyl pyrrolidinone and polyesters.

Other polymers could also be used provided they can be dissolved, cured, or otherwise fixed or polymerized on the sensor housing. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as ethylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers (i.e., carboxymethyl cellulose and hydroxyalkyl celluloses); and combinations thereof. Polyamides for the purpose of this application would also include polyamides of the form —NH—$(CH_2)_n$—CO— and NH—$(CH_2)_x$—NH—CO—$(CH_2)_y$—CO, wherein n is preferably an integer in from 6 to 13; x is an integer in the range of form 6 to 12; and y is an integer in the range of from 4 to 16.

As shown in FIGS. 4A-4E, 5B and 5C, the detector array may be provided on a platform generally shaped as a disc. A representative method for fabrication of a sensor using a detector array disposed on an alumina disc platform is set forth in Example 1; however, the size of the individual electrodes, surface area of the detector platform, and number of detectors present on the platform can vary.

As described, embodiments of the sensor may utilize a minimum of two detectors, arranged in an array configuration. In such embodiments, one detector may be used to detect a background or secondary signal for comparison with a primary signal from another detector, so it can be advantageous to locate these detectors spatially close together. Such an arrangement will allow each detector in such a pair to remain within the same relatively homogenous region of the otherwise heterogeneous tissue, and a space-efficient means to ensure that multiple pairs of detectors can be so disposed is advantageous to minimize the overall size of the sensor.

In embodiments, each detector preferably utilizes a reference, working, and counter electrode that are operatively connected. In order to ensure that the analyte-dependent current flows only between the counter and working electrodes of the same detector in a multi-detector array, it can be desirable to have the electrolyte layer 50 of each detector electrically isolated from that of the other detectors. By arranging the detector array such that each detector shares a common counter electrode, but keeping the electrolyte layer 50 of a detector electrically isolated from the electrolyte layers of other detectors, one can ensure that the current flowing from or to any individual working electrode can be independently monitored and is not confounded by stray currents unrelated to the analyte concentration at that particular detector. Arraying the electrodes with a common counter electrode at the center of the array, the working electrodes arranged radially outboard of the central counter electrode, and the reference electrodes radially outboard of the working electrodes, creates a detector array in which the reference and working electrodes of a single detector can be electrically isolated from the other detectors, close proximity of detectors comprising an operative differential pair may be maintained, and overall size of the array may be minimized.

Figure 4A:
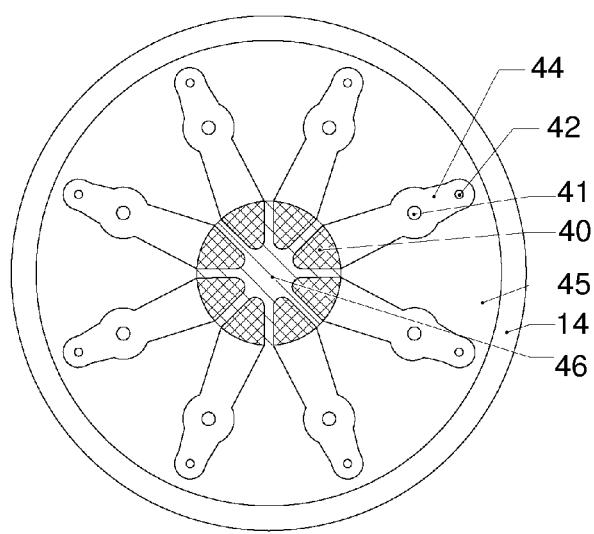
FIG. 4A is a top view of a detector array of a sensor according to an embodiment of the invention. The array is shown with membrane layers removed; a completed detector array includes such membrane layers, which functionalize individual electrode channels for use as substrate detectors of the invention. The array includes eight separate electrode channels disposed in a radial geometry. Each electrode channel includes: a counter electrode 40; working electrode 41; and reference electrode 42. The electrodes are all arranged on an insulating detector array substrate 14. The three electrodes of each electrode channel are disposed within a detector channel well 44, and the perimeter of the detector channel well is defined by insulating material 45. The counter electrode 40 for each channel is provided by exposing, through a window in the insulating material 45, an individual area of a larger common counter electrode patch 46, which is disposed on the substrate 14.
Figure 4B:
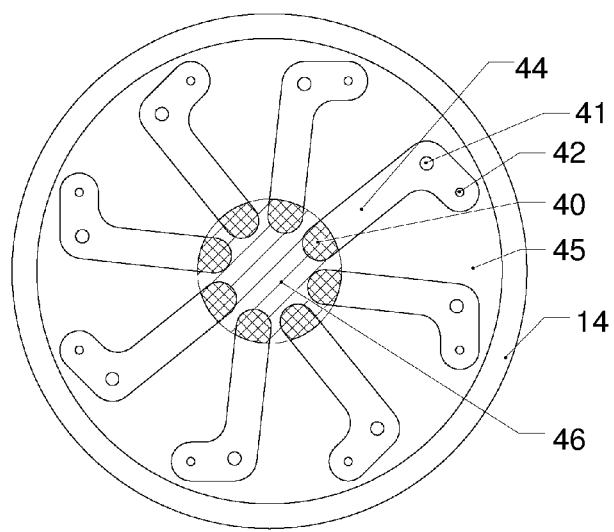
FIG. 4B is a top view of a detector array of a sensor according to an embodiment of the invention. The array is shown with membrane layers removed; a completed detector array includes such layers, which functionalize individual electrode channels for use as substrate detectors of the invention. The array includes eight separate electrode channels. Each electrode channel includes: a counter electrode 40; working electrode 41; and reference electrode 42. The electrodes are all arranged on an insulating detector array substrate 14. The three electrodes of each electrode channel are disposed within a detector channel well 44, and the perimeter of the detector channel well is defined by insulating material 45. The counter electrode 40 for each channel is provided by exposing, through a window in the insulating material 45, an individual area of a larger common counter electrode patch 46, which is disposed on the substrate 14. As shown in this embodiment, the centerline path of the detector channel well 44 need not be linear, but rather may be non-linear and may include curved or angled segments.
Figure 4C:
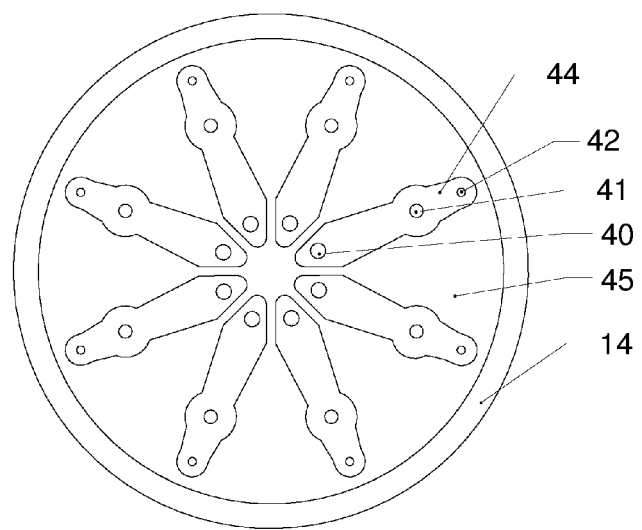
FIG. 4C is a view of a detector array of a sensor according to an embodiment of the invention. The array is shown with membrane layers removed; a completed detector array includes such layers, which functionalize individual electrode channels for use as substrate detectors of the invention. Each electrode channel includes: a counter electrode 40; working electrode 41; and reference electrode 42. The electrodes are all arranged on an insulating detector array substrate 14. The three electrodes of each electrode channel are disposed within a detector channel well 44, and the perimeter of the detector channel well is defined by insulating material 45. The counter electrode 40 for each channel is provided as a separate structure, with no connection to counter electrodes of other channels.

In an embodiment, the central counter electrode is divided using a non-conductive substance on the surface, into zones, each zone being located radially inboard of one working electrode. This radial arrangement is shown in FIGS. 4A-4C. This arrangement facilitates detector independence, as an electrolyte can be positioned to connect one such zone of the counter electrode and the working and reference electrodes outboard of it. After placing a non-conductive, but analyte-permeable, layer 51 over the electrolyte, there is no direct current path between a reference or working electrode and any other electrode structure other than its corresponding counter electrode zone. This radial array is very space efficient and ensures that the working electrodes in a differential pair remain in close proximity and are minimally affected by any analyte heterogeneity that may be present in the tissue.

Typically, as shown in FIGS. 4A-4E, it is desirable to arrange the counter, reference, and working electrodes of a detector channel such that the reference electrode is not located in the path of the ionic current that flows during sensor operation between the counter and working electrode. Additionally, as shown in FIGS. 4A-4D, it is typically further desirable to locate the reference electrode such that its ionic contact with the working electrode is caused to occur such that electrochemical potentials (with respect to the working electrode) that are measured by the reference electrode are not affected significantly by voltage gradients that may be present between the counter and working electrode in the electrolyte layer as a result of such operational ionic current flows (such gradients are referred to in the art as "IR drop"). Arrangements as shown in FIGS. 4A-4D, where the ionic path between the reference electrode and the working electrode does not overlap to a significant extent the ionic path between the working and counter electrodes (such that the influence of IR drop on the measured reference voltage is prevented from exceeding about 100 mV) are preferred.

Figure 4D:
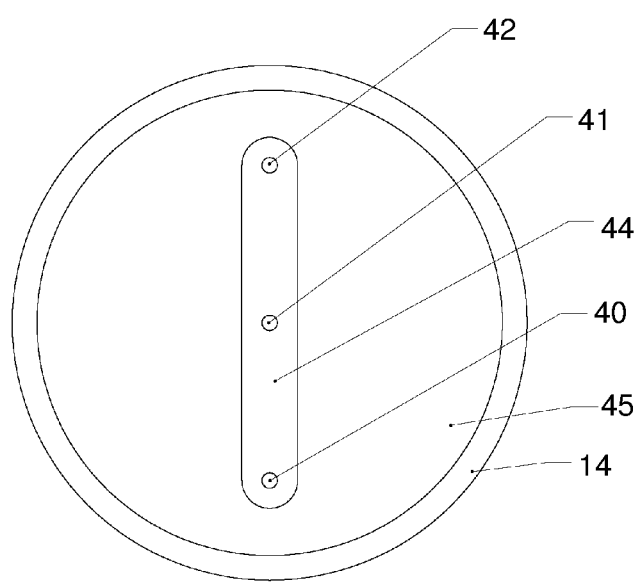
FIG. 4D is a view of a detector array of a sensor according to an embodiment of the invention. The array is shown with membrane layers removed; a completed detector array includes such layers, which functionalize individual electrode channels for use as substrate detectors of the invention. The array comprises a single electrode channel, with elements of the electrode channel arranged in a linear geometry. The electrode channel includes: a counter electrode 40; working electrode 41; and reference electrode 42. The electrodes are all arranged on an insulating detector array substrate 14. The three electrodes of each electrode channel are disposed within a detector channel well 44, and the perimeter of the detector channel well is defined by insulating material 45.

In addition to arrays that include a plurality of detector channels, embodiments with a single channel are also possible, and an example is shown in FIG. 4D. This configuration is depicted with a single counter, working, and reference electrode.

Figure 4E:
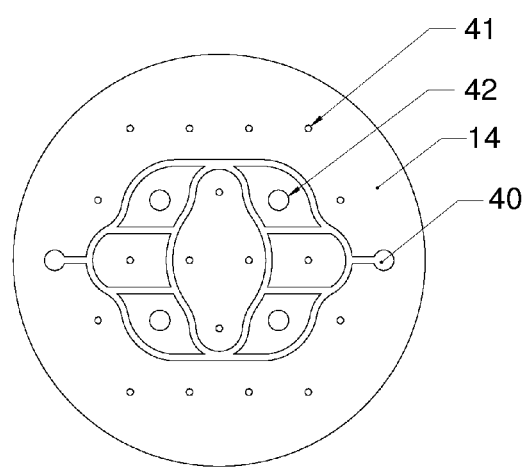
FIG. 4E is a view of a detector array of a sensor according to an embodiment of the invention. The array is shown with membrane layers removed; a completed detector array includes such layers, which functionalize individual electrode channels for use as substrate detectors of the invention. The array includes eighteen separate electrode channels disposed in a grid-pattern geometry. The array includes: a counter electrode 40; working electrodes 41; and reference electrodes 42. The electrodes are all arranged on an insulating detector array substrate 14. The counter electrode 40 for all channels is shared and is provided by a single conductive structure. A total of four reference electrodes 42 are provided, and each reference electrode is utilized by working electrodes in its vicinity.

In addition to the radially arranged array, other array geometries may also be utilized. For example, detectors may be arranged in grid formats. In an array of electrochemical detectors, such a grid may include a central counter electrode that is associated with a gridded plot of working electrodes, or arranged linearly. Also, embodiments where each detector electrode channel is not electrically isolated from other channels, and/or where certain reference electrodes (excepting working electrodes) are shared among channels are also possible. FIG. 4E depicts an array arrangement which includes a plurality of working electrodes, a common counter electrode arranged in a tortuous path, and a set of reference electrodes where an individual reference electrode is utilized by more than one electrode channel.

As will be evident to those skilled in the art, numerous other detector array arrangements could be utilized, including those based on "two-electrode" rather than "three-electrode" electrochemical cell systems, as are depicted in FIGS. 4A-4E. Such two-electrode systems combine the functionality of the reference and counter electrodes into a common electrode. Additionally, as discussed above, non-electrochemical detectors, based on electrical, optical, mechanical, thermal, or other principles as generally known in the art can be employed.

In certain embodiments of the invention, a multiplicity of detectors, preferably spaced at the minimum distance necessary to ensure their independent operation without interference from neighbors, are disposed across the sensor surface in an array or other suitable pattern.

Each detector may have a maximum separation from neighbors limited only by the dimensions of the detector platform, and a maximum diameter as dictated by the power supply to, and power consumption by, the sensor. Typically, detectors will be separated by distances up to or exceeding typical capillary separation distances of ~20 to 500 µm.

For use in tissues where the detectors will be located at some distance from the capillary, arteriole, and venule sources of blood solutes (either because few such sources are present in the tissue, or because placement of the detector portion of the sensor directly adjacent to a vascular bed cannot be assured), the combined surface area of the detectors may be large compared to the length and width of the adjacent vascular bed. The relatively large surface area covered by the multiplicity of detectors increases the probability that one or more detectors will always have reliable access to the tissue microvasculature, notwithstanding changes in the vascular structure and condition. Smaller detectors (in which the combined surface area of the detectors is small compared to the length and width of the vascular source) will be suitable for use where detectors may be placed adjacent to individual capillaries or arterioles.

The dimensions and overall shape of the housing may be adjusted so as to accommodate a variety of internal component configurations. In various embodiments, the housing must remain sufficiently compact and have an overall shape suitable for long term implantation. While a number of shapes may be envisioned for use with the device, an overall shape having a generally planar, three-dimensional geometry is preferable. For example, in one embodiment the housing may be of a discus or puck shape as depicted in FIG. 1A. In other embodiments the housing may be generally elongate and thin as depicted in FIGS. 2A, 2B, 3A, and 3C. In such embodiments, the housing is defined by a major dimension, e.g., length, a minor dimension, e.g., the width, and a thickness. In preferred embodiments, the major and minor dimensions are no greater than 5 cm, and the thickness is no greater than 2 cm. For example, the major and/or minor dimensions may be 3.5 cm, while the thickness may be 1 cm. In various embodiments, the minor dimension and thickness are each less than 75, 65, 60, 50, 40, 30 or even 25% that of the major dimension.

As discussed herein, the sensor is biocompatible to allow for long term implantation into biological tissue. As such, all material used to construct the housing is biocompatible. A variety of suitable medical grade materials are known in the art which may be utilized to construct the housing. In some embodiments, housing portions of the sensor can be made of a metallic material or an alloy such as, but not limited to, bio-inert metals, cobalt-chromium alloys, alloys of cobalt, nickel, chromium and molybdenum, stainless steel, tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Housings can also be constructed from biocompatible ceramic materials, comprising oxides, carbides, borides, nitrides, and silicides of aluminum, zirconium, beryllium, silicon, titanium, yttrium, hafnium, magnesium and zinc. Devices may also be made from biocompatible, biostable polymers, such as polymers including but not limited to fluorpolymers, epoxy resins, polyetherimides, poly ether ether ketone, polysulfone, polyphenylsulfone, polypropylene, polycarbonate, poly methyl methacrylate, and others.

The sensor membrane materials are biocompatible by standard in vitro biocompatibility tests and release few, if any, irritants into the tissue. Use of a pore-free layer (e.g., of PDMS) disposed between the enzyme membrane and electrodes prevents passage of current from the electrodes into the tissues and eliminates possible exacerbation of tissue encapsulation due to electrical flux, which may be a problem for some other implanted sensors.

The components of the sensor may be arranged within or upon the housing in a number of configurations. Various configurations may provide benefits as to functionality of individual components of the sensor. FIGS. 1A, 1B, 2A, 2B, 3A, and 3B depict embodiments where the telemetry transmission portal is integral with or adjacent a wall of the housing such that upon implantation signal transfer efficiency may be increased when the telemetry portal is oriented toward the skin. Additionally, the detector array must be positioned such that the detectors of the array may be in operable contact with the surrounding biological environment such that analyte detection may occur. As such, at least a portion of the detector array must be disposed on a wall of the housing. In some embodiments, to maximize space, and to minimize the chances for interference between the telemetry signals and the low-level detector signals, the telemetry transmission portal and the detector array are opposably positioned within the housing as shown in FIGS. 1B and 3B.

As previously noted, one or more electronics modules may also be disposed within the housing. The electronics modules may be disposed on the same or different planar substrates. FIG. 1B depicts an embodiment in which two electronics modules are disposed within the housing, each on a separate planar substrate.

It has been determined that shielding sensitive electronics modules from electrical interference, i.e. electrical "noise," that may be produced by other electronic modules or other components of the device, enhances functionality of components of the device. As such, in various embodiments, transmission of electrical interference between electronics modules is inhibited or blocked by a partially or entirely interposed conductive substrate or other conductive shielding structure. One advantageous result that is produced by shielding is that the repeatability of measurement of low-level sensor signals is enhanced.

FIGS. 1B and 3B show embodiments in which a conductive substrate is interposed between electronics modules. In FIG. 1B, the electronics modules are each positioned on opposing sides of the battery which may be constructed of material capable of blocking or inhibiting electrical noise or interference, and which is further mounted on a conductive substrate that increases the coverage of the shielding between the electronics modules. As such, the electronics modules and interposed mounted battery are positioned between the detector array and the telemetry transmission portal which are each disposed on opposing walls of the housing.

FIG. 3B shows an alternative embodiment in which the electronics modules are disposed on opposed sides of an interposed conductive substrate, which may have multiple layers, at least one layer of which comprises a material capable of blocking or inhibiting electrical noise or interference. In such embodiments the battery may be positioned adjacent the interposed conductive substrate allowing for an overall housing geometry that is elongated but thinner as compared to that in FIGS. 1A and 1B. As such, the electronics modules and interposed conductive substrate are positioned between the detector array and the telemetry transmission portal, which are each disposed on opposing walls of the housing with the battery being positioned adjacent the interposed conductive substrate.

As pointed out previously, the overall arrangement of components shown in the various embodiments of FIGS. 1A, 2A, 2B, 3A, and 3C, results in a compact elongate planar or discus shape that allows separation and positioning of components to increase performance of the individual components while maintaining a compact geometry suitable for long term implantation. Thus in various embodiments, one or more of the telemetry transmission portal, electronics modules, interposed conductive substrate and/or battery, and detector array are oriented substantially parallel to the major dimension of the housing. In at least one embodiment, the telemetry transmission portal, electronics modules, interposed conductive substrate and/or battery, and detector array are all oriented substantially parallel to the major dimension of the housing.

When inhibition of electrical noise and interference is desired by use of the interposed conductive substrate and/or battery, the components must be constructed of a material suitable to achieve such a result. Many such materials are known in the art and envisioned for use in the present device. Such materials may include various metals including but not limited to copper, brass, aluminum, titanium, tin, gold, silver, and various alloys and mixtures. Suitable such metallic materials may be provided in various forms, including but not limited to metals disposed by plating onto metallic or non-metallic substrates or metal particles disposed in or on polymer, ceramic, or glass carriers. While the conductive substrate may be entirely interposed between the electronics modules, in some embodiments it may be only partially interposed. Alternatively, the conductive substrate may be constructed of a plurality of materials that have differing shielding properties along its length to produce regions of shielding and regions of non-shielding.

As previously noted, the sensor housing is hermetically sealed to be substantially impermeable to moisture at ambient pressures present in body tissues. Depending on the material used, sealing may be performed by brazing or welding; e.g., through use of a high-energy laser or electron beam to raise the temperature of the material to become molten, creating an alloy which is rapidly cooled to create the weld. Preferably, the sealing process is conducted in two or more separate steps. In a first step, a brazing process (or other process requiring that the full extent of the workpieces be subjected to high temperatures) is utilized to hermetically join the ceramic detector array substrate and telemetry portal to their respective metal housing components. This process is preferably performed in a first step to enable its application in the absence of other sensor components that cannot withstand the high temperatures involved. Following this first step, additional sensor components (e.g. electronics, battery) are added to the assembly, and sealing processes that require only localized heating (e.g. laser or electron beam welding) are utilized to provide a final seal to the housing in one or more steps. In certain embodiments, the first step involves the joining of the ceramic substrate and/or telemetry transmission portal to flanges, which flanges are then joined to the their respective metal housing components by an additional joining process involving localized heating of portions of the housing at discrete regions in contact with the flange where the seal is generated.

As such, in another aspect, the present invention provides a method of manufacturing the medical device of the disclosure. The method includes generating a hermetic seal between the housing or housing flange and a ceramic substrate of the detector array, or between the housing or housing flange and the telemetry transmission portal via application of a first joining process. Subsequently, a hermetic seal is generated between at least two portions of the housing, e.g., a top portion and bottom portion, or a bottom portion and a detector array flange and a top portion, via application of a second joining process. The resulting housing is hermetically sealed. As discussed above, the two step process allows components that cannot withstand the first welding procedure to be added between the first and second welding procedures. Thus the method further includes introducing the electrical power source, circuitry, and optionally electronics modules within the housing before application of the second joining process.

The first joining process is performed by generalized heating of certain components of the device including, for example, the housing or housing flange and the telemetry transmission portal to produce the seal. Such components are capable of withstanding generalized heating of the components produced by such processes as brazing, furnacing, and torching. As is known in the art, in a brazing operation, a third material, the "braze material," is introduced to the space between the components to be joined and the braze material is caused to melt and then solidify to accomplish the joining operation. As is also known in the art, wetting of ceramic components by the braze material may be aided by pre-metallizing the ceramic surface using a process such as sputtering. Typical suitable braze materials include but are not limited to gold and other precious metals, as well as alloys of gold with other metals including nickel.

The second joining process is performed by localized heating of the portions of the housing only at discrete regions where the hermetic seal is to be generated which avoids damage to electronic circuitry and the like which cannot withstand elevated temperatures. The second joining process may be performed by methods in which energy having a high power density (on the order of 1 MW/cm$^2$) is applied, resulting in small heat-affected zones and high heating and cooling rates, such as laser or electron beam welding.

In another aspect, the invention provides a method of monitoring glucose level in a subject. The method includes a) implanting a sensor of the invention into a tissue of the subject; b) detecting sensor signals indicative of a glucose level in the subject; and c) wirelessly transmitting the sensor signals via a telemetry transmission portal to an external receiver.

In another aspect, the invention provides a method of treating diabetes in a subject. The method includes a) implanting the sensor of the invention into a tissue of the subject; b) continuously monitoring the glucose level in the subject; c) analyzing the glucose level; and d) providing a therapeutic treatment, a therapeutic treatment recommendation, a warning, or combination thereof.

In various embodiments, detecting and transmitting sensor signals is performed nearly continuously for extended durations. For example, glucose levels may be monitored for up to 3, 6, 9, 12, 15, 18 or 24 months without removing the implanted sensor. The sensor may be configured to transmit sensor signals at a predetermined time interval, typically between 30 seconds and 5 minutes, such as every 1, 2, 3, 4 or 5 minutes.

When used to continuously monitor glucose levels, especially for the treatment of diabetes, the glucose level may be used to direct dosing of therapeutic agents such as anti-diabetes drugs, provide warnings of hypo- or hyper-glycemia, provide recommendations regarding diet and exercise or act as an input for infusion pumps, artificial organs, or tissues, such as an artificial pancreas.

The following examples are provided to further illustrate the advantages and features of the present invention, but are not intended to limit the scope of the invention. While they are typical of those that might be used, other procedures, methodologies, or techniques known to those skilled in the art may alternatively be used.

Example I

Functional Analysis of Implanted Tissue Glucose Sensor

Experimental Summary

An implantable sensor of the present invention capable of long term monitoring of tissue glucose concentrations by wireless telemetry was developed for eventual application in humans with diabetes. As discussed further herein, the sensor telemetry system functioned continuously while implanted in subcutaneous tissues of two pigs for a total of 222 and 520 days, respectively, with each animal in both nondiabetic and diabetic states. The sensor detects glucose via an enzyme electrode that is based on differential electrochemical oxygen detection, which thereby reduces the sensitivity of the sensor to encapsulation by the body, variations in local microvascular perfusion, limited availability of tissue oxygen, and inactivation of the enzymes. After an initial 2-week stabilization period, the implanted sensors maintained stability of calibration for extended periods. The lag between blood and tissue glucose concentrations was 11.8±5.7 and 6.5±13.3 minutes (mean±standard deviation), respectively, for rising and falling blood glucose challenges. The lag resulted mainly from glucose mass transfer in the tissues, rather than the intrinsic response of the sensor, and showed no systematic change over implant test periods. These results represent a milestone in the translation of the sensor system to human applications.

Sensor Construction and Design

Eight 300-micron diameter platinum working electrodes, with associated platinum counter electrodes and Ag/AgCl potential reference electrodes were arranged as eight detector channels (i.e. four detector pairs) on the surface of a 1.2-cm-diameter alumina disc. The working, counter, and reference electrode of each detector channel were covered by a thin electrolyte layer, a protective layer of medical-grade silicone rubber (comprising polydimethylsiloxane (PDMS)), and an additional membrane comprising PDMS with wells for the immobilized enzymes glucose oxidase and catalase (both enzymes from $A.\ niger$) located over certain electrodes. The enzymes were immobilized in the wells by crosslinking with albumin using glutaraldehyde, and the resulting gel was rinsed extensively to remove unbound material. Prior to application of the membrane layers, the alumina detector array substrate disc was fused into a titanium housing component (see FIG. 2B), the working and counter electrodes were platinized, the reference electrodes were silver plated, and potentiostat and signal-conditioning circuitry for each detector, a wireless telemetry system, and a battery having a minimum 1-year lifetime were added. Also prior to application of the membrane layers, a matching titanium housing component with hermetically sealed telemetry portal was hermetically joined to the assembly to close the housing. The implant was sterilized with a chemical sterilant by a procedure that was validated according to standard methods (see FDA-accepted consensus standard "ANSI/AAMI/ISO 14160:1998).

As shown in FIG. 1A, the implant is 3.4 cm in diameter and 1.5 cm thick. The top surface of the implant includes two polyester fabric velour patches for tissue adhesion. The cross-sectional schematic view of FIG. 1B shows electronics modules 11, telemetry transmission portal 3, battery 12, and detector array substrate 14.

The sensor's telemetry system samples the currents from individual detectors, encodes the samples into multiplexed signal segments, and transmits the segments as a train of radio-frequency signals at regular 2-min intervals to an external receiver, where the signals are decoded and recorded. The potentiostat circuitry in the implant includes control of eight individual working electrodes. Radio-telemetry was accomplished with a 433.92-MHz carrier signal, with a total effective radiated power of <100 nW, providing a practical effective transmitter range of ~10 feet (3.085 m) with information packet reception rate exceeding 97%. This hermetically sealed wireless telemetry system made possible long term recordings without infection-prone percutaneous electrical leads.

Implantation

Two series of implant studies were conducted. In the first series, intended to aid design optimization and component reliability verification, a total of 30 individual sensor telemetry units were implanted in six nondiabetic pigs to refine the surgical technique, evaluate device tolerance and biocompatibility, test the electronic circuitry and telemetry, and identify factors that affect the lifetime of the sensor. The devices in this series were explanted and analyzed according to preset protocol schedules at periods ranging from 1 to 18 months after implantation. Results from this foundational research included verification of (i) acceptable long term biocompatibility, assessed after 18-month implant periods; (ii) immobilized enzyme life exceeding 1 year; (iii) battery life exceeding 1 year; (iv) electronic circuitry reliability and telemetry performance; (v) sensor mechanical robustness including long term maintenance of hermeticity; (vi) stability of the electrochemical detector structure; and (vii) acceptability and tolerance of the animals to the implanted device. Results were obtained from this series related to the effects of tissue permeability and tissue remodeling and are discussed further below.

In the second series, which involved evaluation in diabetic conditions and which is described in further detail below, two devices were implanted in each of two pigs (four devices total) and first operated for 352 days (subject 1) and 16 days (subject 2), respectively, with the animals in the nondiabetic state. The animals were then made diabetic by administration of streptozotocin, and the devices continued to operate for an additional 168 days in subject 1 to a total of 520 days, and for an additional 206 days in subject 2 to a total of 222 days. Individual experiments were terminated because of the substantial resources required to maintain diabetic animals. No adverse medical events (infection, erosion, migration, etc.) were encountered with any implant in either test series. Together, the test series represent a collective 31 total device-years of implant experience, with 17 of the devices remaining implanted and functional for more than 1 year.

Glucose Sensor Data Recording

Figure 6:
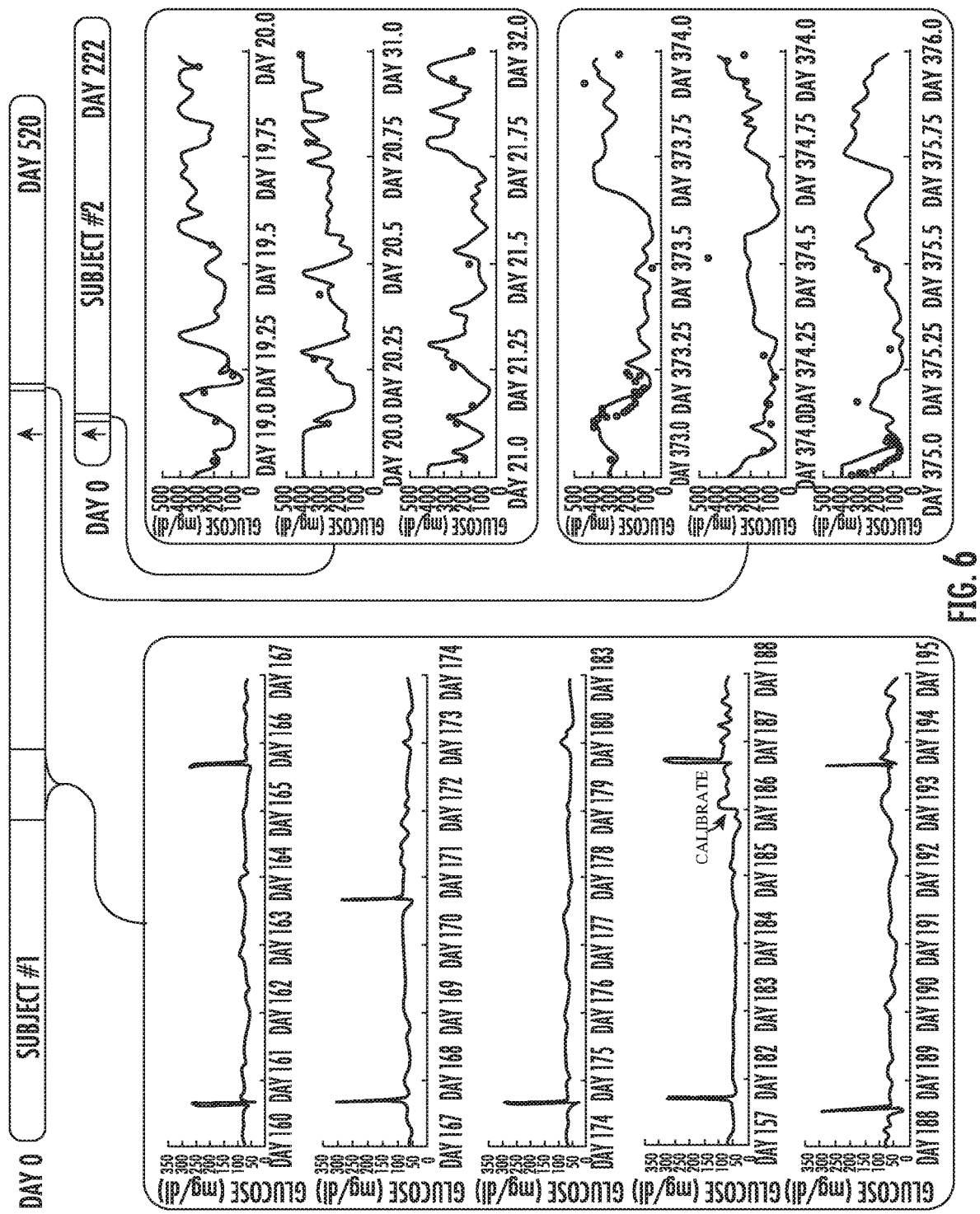
FIG. 6 depicts data obtainable using a sensor of the present disclosure to detect alteration of glucose concentrations in an animal model.

FIG. 6 shows the long term continuous monitoring in nondiabetic and diabetic pigs. Timelines for sensor operation in subjects 1 and 2 are provided at the top; diabetes induction is indicated for each animal by an arrow. Sensor outputs are shown as solid red lines, and plasma glucose values from laboratory analysis of central venous samples are shown as solid blue circles. Left: The displayed 5-week period begins 23 weeks after implantation in subject 1. Plasma glucose values were sampled during intravenous glucose tolerance tests (IVGTTs) administered once or twice weekly to assess the sensitivity to glucose during the nondiabetic phase. Glucose concentrations are relatively stable between IVGTTs in nondiabetic pigs despite eating, and intravenous glucose challenges were required to produce significant glucose excursions. Right: The sensor output is shown over two continuous 3-day periods in two diabetic pigs. In subject 1, the sensor had been operated for 352 days with the animal in the nondiabetic state at the time of induction of diabetes, after which monitoring continued for 168 more days. The segment displayed begins on day 373 after sensor implantation (21 days after conversion of the animal to diabetic). In subject 2, diabetes was induced 16 days after device implantation, after which monitoring continued for another 206 days. The segment displayed begins on day 19 after sensor implantation (3 days after conversion of the animal to diabetic).

In the non-diabetic example shown in FIG. 6, only one system calibration adjustment was performed during the period (on day 186), with the goal of obtaining a qualitative indication of the implanted sensor stability. From that point forward, a fixed calibration regimen with regular calibration adjustment every 10 days was used for analysis of sensor accuracy (see below).

Results after the pigs became diabetic are also shown in FIG. 6. As expected, a considerable difference was noted in the extent and duration of glucose excursions between the nondiabetic and the diabetic states. In the nondiabetic state, glucose concentration remained relatively constant at a baseline of ~75 mg/dl, regardless of feeding and physical activity. As a result, to test the sensor sensitivity to glucose, it was necessary to create blood glucose excursions by intravenous infusion of glucose, resulting in rapid rise and rapid unaided return to the baseline caused by the endogenous insulin response. In the diabetic state however, the blood glucose concentration varied substantially with time, rising and falling in complex response to feeding, activity, and administration of insulin. (Note that the sensor response was electronically "capped" at 400 mg/dl, so glucose values above that level are not reported by the sensor.) Insulin injections were needed regularly to interrupt sustained hyperglycemic episodes.

Sensor Signal Accuracy

The sensor accuracy was assessed on the basis of data collected from glucose excursion tests conducted during the diabetic phase in subjects 1 and 2. Conventional statistical methods were used, including standard regression analysis, error grid plots that segregate results into graphical regions on the basis of potential clinical significance by using both original sensor values and values adjusted for delay (described below), and mean and median absolute relative difference (ARD) analyses. Results obtained from the diabetic animals were as follows (with values retrospectively adjusted for an average 6.6-min delay, determined for the diabetic phase as discussed below, in parentheses): number of points: 392; error grid values: 63.8% (70.4%) of points in region A (error has no effect on clinical action), 32.4% (28.6%) in region B (error is clinically benign), 3.6% (1.0%) in region C (error likely to affect clinical outcome), 0.3% (0%) in region D (error poses medical risk), and 0% (0%) in region E (error is potentially dangerous clinically); ARD values: mean, 22.1% (17.9%); median, 14.7% (13.2%); and correlation coefficient: 0.88 (0.92). These results suggested that, although there may be quantifiable differences between the actual blood glucose concentrations and values reported by the sensor, none of these differences would lead to a mistaken, potentially dangerous clinical action. The results obtained here are comparable to published values obtained for shorter periods from currently available short term continuous glucose monitors used clinically.

Sensor Signal Delay

When sensors are operated continuously, a lag or delay exists during dynamic conditions between the actual blood glucose concentration and the value reported by the sensor. Associated with the delay is the dynamic error, which is the difference between the actual and reported blood glucose values at a given time. The delay and associated error can depend on the intrinsic rate of the sensor response, the rate of glucose mass transfer in the tissues, and the instantaneous rate of blood glucose change of the subject. The component of delay attributable to the sensor is determined from in vitro experiments in which glucose concentration is changed abruptly. The instantaneous rate of blood glucose change is determined by frequent blood glucose sampling, and the rate of glucose mass transfer in the tissues is limiting when the other two processes are much faster.

Figure 7:
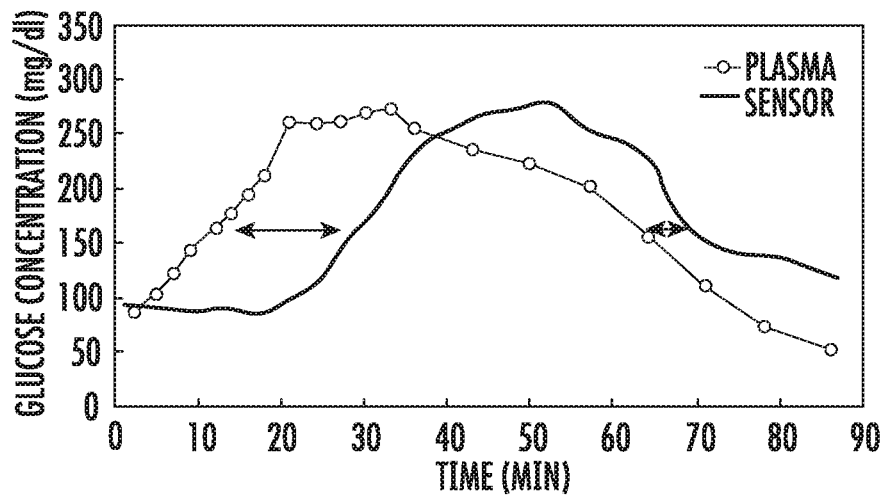
FIG. 7 depicts data obtainable using a sensor of the present disclosure which show examples of sensor response during an intravenous glucose tolerance test (IVGTT) excursion in an animal model as discussed in Example 1. Plasma glucose values in solid circles are connected by the line and the sensor signal is the continuous solid line. The arrows indicate the delay at the 50% points between the minimum and the maximum plasma glucose concentrations for the rising and falling excursions.

The delay in the response to an intravenous glucose tolerance test (IVGTT) in subject 1 on day 168 during the nondiabetic phase is shown in FIG. 7. The maximal rate of glucose rise because of glucose infusion was ~8 mg/dl per minute, and the maximal rate of fall because of endogenous insulin action was 6 mg/dl per minute. After an initial lag, the sensor signal rose at a rate parallel to the plasma glucose ramp. The glucose concentration then remained at a plateau value of ~260 mg/dl created by a reduced glucose infusion rate for ~15 min, before falling toward the baseline, with the sensor signal falling thereafter. During the excursion tests in the diabetic phases, maximal rates of central venous plasma glucose change (mean±SD, n=34) were 4.1±1.9 and 5.2±1.0 mg/dl per minute for rising and falling transitions, respectively. The rates of blood glucose change during testing in the nondiabetic phases were significantly more rapid than the maximal spontaneous rates of change previously reported in diabetic subjects, which are ~3 mg/dl per minute rising and 2.5 mg/dl per minute falling.

The definition of the rising or falling delay used here (shown by the arrows in FIG. 7) is the time between the plasma glucose value and the sensor value at the 50% point between the minimum and maximum plasma glucose values in an excursion. For example, if the minimum plasma glucose value in an excursion was 100 mg/dl (for example, at baseline, before infusion of glucose) and reached a plateau at 200 mg/dl upon glucose infusion, the rising delay is the difference between the time the plasma glucose reaches 150 mg/dl and the time that the sensor indicates 150 mg/dl. The falling delay from each excursion was evaluated during the falling leg at the same 50% plasma glucose crossing point. With this technique, the average value of the rising delay was 11.8±5.7 min (mean±SD) and of the falling delay was 6.5±13.3 min, based on 34 IVGTTs in subject 1 during the nondiabetic period. Of these values, 2.5±1.2 min is ascribable to the sensor itself, as determined from independent in vitro measurements, and an estimated 0.5 min is ascribable to circulatory transport from the central venous infusion site to the implant site. The remainder of the rising and falling average delays (8.8 and 3.5 min, respectively) is attributable to mass transfer and physiologic phenomena within the local tissues. Over the extended implant period, there was no change in either average delay value.

These delay values were confirmed with an alternative approach (as described in Kovatchev et al., *Diabetes Technol. Ther.* 11, 139-143 (2009)) based on systematic retrospective displacement of the sensor signal values with respect to the measured plasma glucose values and determination of the root mean square coefficient of variation between all sensor and plasma values at each step. For the IVGTT data set of subject 1 referenced above, the minimum coefficient of variation value was obtained at a signal displacement of ~10 min, which is comparable to the average of the rising and falling lag values determined as reported above. In the diabetic phase, the minimum coefficient of variation value was obtained at a signal displacement of 6.6 min (average of subjects 1 and 2).

Oxygen Reference Detector

Figure 8:
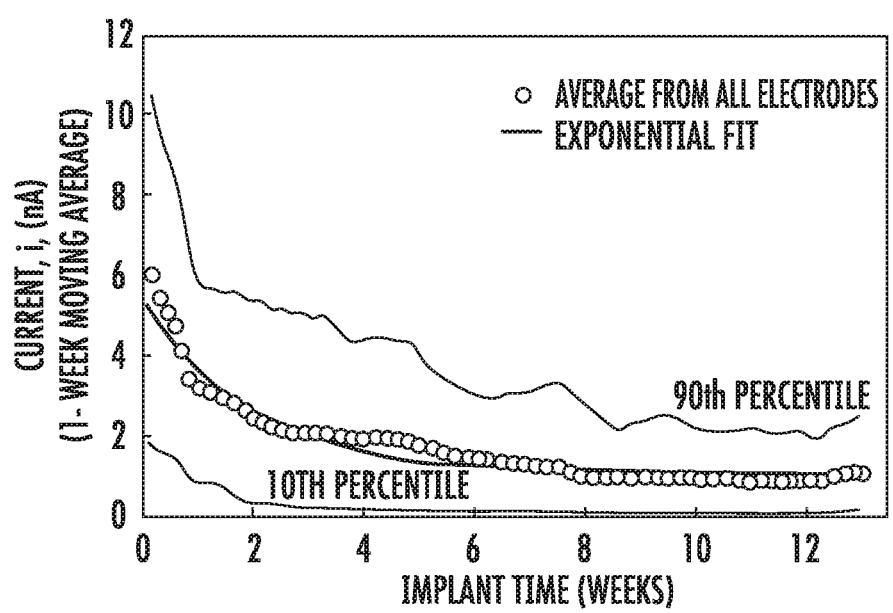
FIG. 8 depicts data obtainable using a sensor of the present disclosure which shows signals from implanted oxygen detectors over 3 months in an animal model. The averaged signal (open circles), expressed as oxygen electrode current in nanoamperes, which is proportional to the permeability of the foreign body tissue to oxygen, decays exponentially, approaching an asymptotic constant value at ~6 weeks. The exponential fit (black line) is provided by $i_o = a \exp(-bt) + c$, where $a = 4.5$ nA, $b = 0.49$ week$^{-1}$, $c = 1.0$ nA, and $R^2 = 0.96$. Each data point is an average of the signals from 60 electrodes. Data comprising the 10th and 90th percentiles are represented by the lower and upper lines, respectively.
Figure 9:
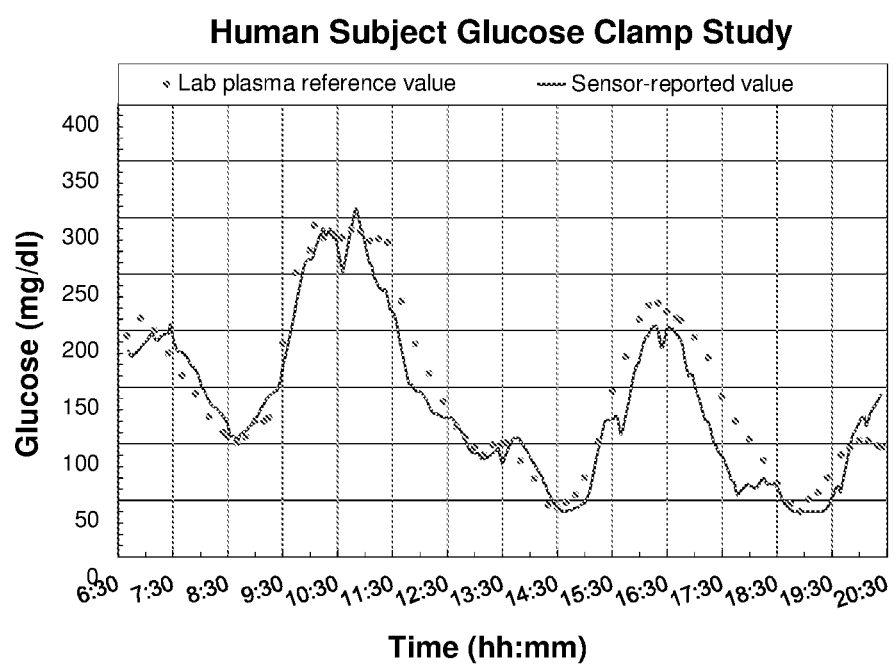
FIG. 9 depicts data obtainable using a sensor of the present disclosure to detect alteration of glucose concentrations in a human. The data were obtained from a sensor of the invention after five months of continuous operation in a diabetic human subject. Plasma glucose values determined by a laboratory reference standard method are shown in solid circles and the sensor signal is the continuous solid line.

Signals from the oxygen reference detector indicate the time course of change in tissue permeability after implantation. The averaged signals from the oxygen reference detectors from the series of implanted animals are plotted as a function of implant time in weeks (FIG. 8). Each data point (open circle) represents an average of 60 detector signals at the indicated time after implantation, and points are fitted to an exponential decay curve (black line). It is noteworthy that the averaged oxygen signals decayed exponentially, asymptotically approaching a nonzero value within ~6 weeks, and remain relatively constant thereafter. Previous studies with hamsters showed that the exponential signal decay is due to changes in the effective permeability of the tissue, rather than changes in the sensitivity of the detectors per se. This was demonstrated by comparison of pre-implantation and post-explantation measurements of detector sensitivity to oxygen in the gas phase, where boundary layers are absent and highly precise measurements are possible. Thus, the decay of both the oxygen reference signal and the oxygen component of the glucose detector signal was due to changes in the effective permeability of the tissue, which stabilizes within several weeks.

The observation that the sensitivity to glucose remained stable during a period of significant oxygen signal decay reveals an advantage of the sensor design. The glucose-sensing strategy of the sensor, which is based on differential oxygen detection, reduced the sensitivity of the glucose-dependent signal to tissue encapsulation by the foreign body response to the implant. Because the substrate sensitivity of both oxygen and glucose detectors decayed in parallel as the effective tissue permeability decreased after implantation, the glucose-dependent difference signal remained largely unaffected.

Design for Long Term Operation

The preferred embodiment whose construction is illustrated above has several important design features that make possible long term operation in the tissue environment. First, glucose oxidase is specific for glucose over other biochemicals present in tissue fluids. Second, there is a nonporous layer (PDMS in the above example) between the enzyme membrane and the electrodes, which allows oxygen passage by solubilization in its hydrophobic phase but prevents electrode poisoning and interference from polar endogenous biochemicals and common exogenous chemicals such as acetaminophen and ascorbic acid. Third, the electrochemical oxygen detectors are based on the three-electrode potentiostatic principle and retain long term stability of oxygen sensitivity, in contrast to some conventional oxygen detector systems. Fourth, glucose oxidase is inactivated by hydrogen peroxide, the catalytic product, but the lifetime of the immobilized glucose oxidase is extended by including coimmobilized catalase in excess to prevent peroxide-mediated inactivation and by incorporating a large reserve of the enzymes to maintain a diffusion-limited design. These features have not been feasible in other glucose sensor designs based on electrochemical detection of hydrogen peroxide.

Minimization of Tissue Irritation

The acceptable level of tissue permeability adjacent to the sensor may also be due, in part, to several design features of the sensor. The sensor membrane materials are biocompatible by standard in vitro biocompatibility tests and release few, if any, irritants into the tissue. The pore-free PDMS layer prevents passage of current from the electrodes into the tissues and eliminates possible exacerbation of tissue encapsulation due to electrical flux, which may be a problem for some other implanted sensors. In the preferred embodiment, catalase consumes peroxide, which would otherwise diffuse into adjacent tissues and cause strong irritation. Inclusion of catalase is not possible in other enzyme electrode sensors that are based on hydrogen peroxide detection.

Oxygen Access

The stoichiometric shortage of oxygen in tissues with respect to glucose, known as the oxygen deficit, can be two or more orders of magnitude. If not resolved, this discrepancy would cause the enzyme reaction in the sensor to be limited by oxygen rather than glucose, and the range of sensitivity to glucose to be substantially reduced. Our sensor design avoids this problem both by salvaging one-half equivalent of oxygen from hydrogen peroxide via the catalase reaction and by controlling the relative access of substrates to the enzyme region by a novel "two-dimensional" membrane design (as disclosed in U.S. Pat. No. 7,336,984, incorporated herein by reference), which permits both radial and axial diffusion of oxygen but only axial diffusion of glucose into the immobilized enzyme gel. These features allow the sensor to respond to glucose over a clinically useful concentration range even at very low tissue oxygen concentrations.

Variable Microvascular Perfusion

The signals of individual detectors are affected by convection and diffusion of the substrates, in addition to their concentrations in blood. In tissues, glucose and oxygen are conveyed to the implant site by blood that perfuses the regional microvasculature, and then diffuse from capillaries to each detector. Physiologic variations in blood flow associated with exercise, sleep, movement, hydrostatic changes, and local temperature changes affect the oxygen flux to both the glucose and the oxygen reference detectors simultaneously, as do tissue permeability variations, but the signal artifacts associated with these common physiological events are largely subtracted by the differential oxygen detector design disclosed herein.

Regardless of their respective concentrations in blood, glucose and oxygen are distributed heterogeneously in tissues at the microscopic level. As shown in FIG. 8, there is a broad range of oxygen detector signals between the 10th and the 90th percentile limits. Although oxygen detectors are uniform in fabrication and produce near-identical signals in vitro, when implanted, the detectors produce a range of signal values because of the specific microvascular pattern in the immediate neighborhood of each detector. The array of paired glucose and oxygen detectors in the implant provides a means for averaging these local spatial distributions of the substrates to enhance the accuracy of glucose measurement by the sensor.

Sensor Dynamic Response

A key question is whether an implanted sensor can respond fast enough to follow physiologic blood glucose changes. For the sensor of the invention, in which the response of the sensor per se is rapid relative to glucose mass transfer within the tissues, the overall rate of response depends on achieving minimal tissue encapsulation/maintaining adequate tissue permeability.

For glucose monitoring based on discrete blood sampling, it has been reported that regular sampling at most every 12 to 15 min is necessary and sufficient to accurately reconstruct the most rapid physiologic blood glucose excursions, according to the classic Shannon-Nyquist sampling criterion (two regularly spaced samples per cycle of the most rapid frequency component). This suggests that a continuously operated sensor having a maximal 12- to 15-min delay could be effective in capturing blood glucose excursions. The average 11.8-min rising and 6.5-min falling delays seen with this sensor are well within this criterion, indicating that, on average, this system is capable of following the most rapid blood glucose excursions expected in diabetic subjects and, by extension, more typical slower excursions as well.

It has also been reported that autoregressive moving-average methods based on previous blood glucose measurements can predict blood glucose values ahead of real time by as much as 20 min with quantifiable accuracy. This strategy could be used with the sensor to further mitigate the effects of delay, if necessary in later applications.

For potential use with an artificial pancreas, the sensor described here responds relatively rapidly compared to the other components of a closed-loop system, namely, the serial processes of insulin delivery from a pump to a tissue site, insulin adsorption into blood (which, by itself, may be slow relative to the sensor), circulation of insulin and glucose to the peripheral tissues, and activation of the blood glucose change. Therefore, the sensor can have a key role in use of the artificial pancreas to counter hyperglycemic excursions. The convenience of a long term, fully implanted sensor may also make an artificial pancreas more acceptable to a larger group of people with diabetes. Further, the ability of the sensor to detect and warn of hypoglycemia in a timely fashion will potentially increase the safety of automatic blood glucose control systems.

It has been shown that, with appropriate design, an implanted glucose sensor can potentially operate effectively for long periods in the body. These experimental results and the understanding of the sensor function derived from animal studies provide a foundation for translation to human clinical investigation.

For more detailed explanation, the following experimental methods were utilized throughout the above experiments with the sensor described.

Device Implantation

Individual sensors were implanted in subcutaneous tissue sites in 20-kg anesthetized Yucatan minipigs by making an incision 5 cm long and 0.5 to 1 cm deep, retracting the skin, and exposing the dermal layers. A pocket was created between the subdermal fat and underlying muscle with blunt dissection while not disturbing the fascia. The implants were placed in this pocket with the sensor surface facing inward toward the muscle layer. Small polyester velour pads were previously fixed to the implant surface to reduce the potential for implant migration. Once the implant was seated in the pocket, the incision was sutured and the animal was wrapped with a protective bandage. A modified dual-lumen Hickman catheter (Bard Access Systems) was introduced into the central vena cava for blood sampling and fluid infusion, with the catheter ports exteriorized at the midscapular region. The catheter was maintained patent between uses with a dilute solution of heparin. Sterile technique was used in the procedures, and the National Institutes of Health Guide for the Care and Use of Laboratory Animals was followed for all animal activities.

Glucose Excursion Tests

Glucose excursion tests were performed once or twice weekly. Glucose excursions were achieved by intravenous glucose tolerance tests (IVGTTs) administered by controlled central venous infusion of a 50% glucose solution. In nondiabetic animals, a concomitant infusion of a somatostatin analog (Bachem) was used to partially suppress endogenous insulin production. The results were blood glucose excursions that included a rapid rise from the normoglycemic value (~70 mg/dl) to a plateau of ~250 mg/dl, a dwell at the plateau value for ~20 min, and then a rapid unaided fall to the baseline because of the action of endogenous insulin, with occasional mild hypoglycemic undershoot. In diabetic animals, an intravenous insulin bolus was typically used to acutely drop blood levels from starting values of between 200 and 250 mg/dl to nadirs of between 50 and 100 mg/dl, in addition to IVGTT. Central venous blood was sampled every 5 to 10 min during excursions, and central venous plasma glucose values were determined with a Yellow Springs Instrument Company (YSI) 2300 STAT Plus glucose analyzer.

Conversion to Diabetes Condition in an Animal Model

Pigs were made diabetic by infusion of streptozotocin (85 mg/kg) (Axxora). After conversion, animals were maintained on multiple daily subcutaneous and intravenous injections of insulin at typically 0.3 to 0.7 U/kg per day. Blood glucose samples were obtained frequently during the first day after induction of diabetes to assure avoidance of severe hypoglycemia, and multiple times daily thereafter.

Sensor Calibration

As an optimum calibration interval was not known a priori, a protocol based on a fixed 10-day interval was used with glucose excursions for sensor calibration. The least-squares error between the sensor output and YSI assays of central venous plasma samples was used to determine the values of $k_1$ and $k_2$, and the resulting calibration was then used for the following 10 days. Correlation data obtained during a sensor response to a "calibration excursion" were not included in the accuracy determinations. The statistical analyses included only data collected during the sensor responses on days subsequent to calibrations.

Although the invention has been described with reference to the above example, it will be understood that modifications and variations are encompassed within the spirit and scope of the invention. Accordingly, the invention is limited only by the following claims.

What is claimed is:

1. An implantable analyte sensor, comprising:
   a biocompatible hermetically sealed housing having a size and shape suitable for implantation in tissues of a body of a subject;
   a detector array comprising at least one detector and at least one membrane layer, the at least one membrane layer comprising at least:
      an enzymatic material; and
      a membrane structure comprising at least a cavity, the enzymatic material disposed within the cavity;
   an electrical power source;
   circuitry operatively connected to the detector array and configured to process at least a portion of signals generated by the at least one detector for generation of processed detector signals; and
   a telemetry transmission portal configured for wireless communication with an external receiver outside of the tissues of the body when the implantable analyte sensor is implanted subcutaneously;
   wherein the electrical power source and the circuitry are disposed within the housing, and the detector array and the telemetry transmission portal are disposed within or upon the housing;
   wherein the at least one detector comprises a plurality of detectors;
   wherein the detector array further comprises at least one electrolyte layer, at least a portion of the at least one electrolyte layer disposed between the plurality of detectors and the at least one membrane layer; and
   wherein the membrane structure further comprises: (i) a bottom wall, (ii) a top wall opposing the bottom wall, (iii) at least one side wall connected to each of the bottom wall and the top wall, the bottom wall, the top wall and the at least one side wall defining the cavity, and (iv) an aperture disposed in the top wall and in communication with the cavity, a non-enzymatic cross-linked protein material disposed within the aperture.

2. The implantable analyte sensor of claim 1, wherein the non-enzymatic cross-linked protein material is configured to occlude the aperture and enclose the enzymatic material within the cavity.

3. The implantable analyte sensor of claim 1, wherein the bottom wall of the membrane structure is disposed between the at least one electrolyte layer and the enzymatic material.

4. The implantable analyte sensor of claim 1, wherein:
the implantable analyte sensor is configured for detection of blood glucose; and
the enzymatic material comprises a crosslinked protein material having at least two types of enzyme co-immobilized therein, the at least two types of enzyme comprising at least glucose oxidase (GO) and catalase.

5. The implantable analyte sensor of claim 4, wherein the glucose oxidase is immobilized within the crosslinked protein material at a first concentration, and the catalase is immobilized within the cross-linked protein material at a second concentration, the first concentration selected for a desired detector response time characteristic, the second concentration selected to be in excess relative to the first concentration in order to limit degradation of the glucose oxidase caused by exposure to a hydrogen peroxide byproduct, the hydrogen peroxide byproduct produced during a reaction between the glucose oxidase and the blood glucose when the implantable analyte sensor is implanted subcutaneously.

6. The implantable analyte sensor of claim 1, wherein the at least one membrane layer comprises one or more three-dimensional portions which protrude above an outer surface of the biocompatible hermetically sealed housing, the one or more three-dimensional portions configured to promote interlock with the tissues of the body when the implantable analyte sensor is implanted subcutaneously.

7. The implantable analyte sensor of claim 6, wherein each of the one or more three-dimensional portions comprises at least an outer surface of the least one membrane layer, at least a portion of the outer surface comprising a textured surface.

8. The implantable analyte sensor of claim 6, wherein each of the one or more three-dimensional portions comprises a disc-shaped membrane structure, the disc-shaped membrane structure having a diameter that is greater than a height thereof.

9. The implantable analyte sensor of claim 1, wherein the non-enzymatic cross-linked protein material is configured to occlude the aperture and enable diffusion of analyte from the tissues of the body into the cavity for reaction with the enzymatic material when the implantable analyte sensor is implanted subcutaneously.

10. The implantable analyte sensor of claim 9, wherein a thickness of the non-enzymatic crosslinked protein material is selected for a desired analyte permeability characteristic.

11. The implantable analyte sensor of claim 9, wherein a thickness of the non-enzymatic crosslinked protein material is selected for a desired detector response time characteristic.

12. The implantable analyte sensor of claim 9, wherein:
the enzymatic material comprises a crosslinked protein material having at least glucose oxidase (GO) immobilized therein; and
the non-enzymatic crosslinked protein material is formed on a top surface of the crosslinked protein material having at least glucose oxidase (GO) immobilized therein.

13. The implantable analyte sensor of claim 1, wherein:
the circuitry is further configured to generate data related a blood analyte level measurement based at least on a portion of the processed detector signals; and
the telemetry transmission portal is configured to transmit the data related to the blood analyte level to the external receiver.

14. An implantable blood glucose sensor, comprising:
a biocompatible hermetically sealed housing having a size and shape suitable for implantation in tissues of a body of a subject;
a detector array comprising at least one detector and at least one membrane layer, the at least one membrane layer comprising at least:
an enzymatic material comprising a cross-linked protein material having glucose oxidase and catalase co-immobilized therein;
a membrane structure comprising at least a cavity and an aperture, the aperture in communication with the cavity;
a non-enzymatic cross-linked protein material disposed within the aperture, the membrane structure and the non-enzymatic cross-linked protein material configured to enclose the enzymatic material within the cavity; and
an electrolyte layer disposed between the at least one detector and the membrane structure;
an electrical power source;
circuitry operatively connected to the detector array and configured to process at least a portion of signals generated by the at least one detector for generation of processed detector signals; and
a telemetry transmission portal configured for wireless communication with an external receiver outside of the tissues of the body when the implantable blood glucose sensor is implanted subcutaneously;
wherein the electrical power source and the circuitry are disposed within the housing, and the detector array and the telemetry transmission portal are disposed within or upon the housing.

15. The implantable blood glucose sensor of claim 14, wherein a thickness of the non-enzymatic crosslinked protein material is selected for a desired glucose permeability characteristic.

16. The implantable blood glucose sensor of claim 14, wherein a thickness of the non-enzymatic crosslinked protein material is selected for a desired detector response time characteristic.

17. The implantable blood glucose sensor of claim 14, wherein the glucose oxidase is immobilized within the crosslinked protein material at a first concentration, and the catalase is immobilized within the cross-linked protein material at a second concentration, the first concentration selected for a desired detector response time characteristic, the second concentration selected to be in excess relative to the first concentration in order to limit degradation of the glucose oxidase caused by exposure to a hydrogen peroxide byproduct, the hydrogen peroxide byproduct produced during a reaction between the glucose oxidase and the blood glucose when the implantable blood glucose sensor is implanted subcutaneously.

18. The implantable blood glucose sensor of claim 14, wherein the at least one membrane layer comprises one or more three-dimensional portions which protrude above an outer surface of the biocompatible hermetically sealed housing, the one or more three-dimensional portions configured to promote interlock with the tissues of the body when the implantable analyte sensor is implanted subcutaneously.

19. An implantable analyte sensor, comprising:
a biocompatible hermetically sealed housing having a size and shape suitable for implantation in tissues of a body of a subject;
a detector array comprising at least one detector and at least one membrane layer, the at least one membrane layer comprising at least:
an enzymatic material; and
a membrane structure comprising at least a cavity, the enzymatic material disposed within the cavity;
an electrical power source;
circuitry operatively connected to the detector array and configured to process at least a portion of signals generated by the at least one detector for generation of processed detector signals; and
a telemetry transmission portal configured for wireless communication with an external receiver outside of the tissues of the body when the implantable analyte sensor is implanted subcutaneously;
wherein the electrical power source and the circuitry are disposed within the housing, and the detector array and the telemetry transmission portal are disposed within or upon the housing; and
wherein the membrane structure further comprises an aperture in communication with the cavity, the aperture having a non-enzymatic crosslinked protein material disposed therein, the non-enzymatic cross-linked protein material configured to occlude the aperture and enable diffusion of analyte from the tissues of the body into the cavity for reaction with the enzymatic material when the implantable analyte sensor is implanted subcutaneously.

20. The implantable analyte sensor of claim 19, wherein a thickness of the non-enzymatic crosslinked protein material is selected for a desired analyte permeability characteristic.

21. The implantable analyte sensor of claim 19, wherein a thickness of the non-enzymatic crosslinked protein material is selected for a desired detector response time characteristic.

22. The implantable analyte sensor of claim 19, wherein:
the enzymatic material comprises a crosslinked protein material having at least glucose oxidase (GO) immobilized therein; and
the non-enzymatic crosslinked protein material is formed on a top surface of the crosslinked protein material having at least glucose oxidase (GO) immobilized therein.

23. The implantable analyte sensor of claim 19, wherein:
the circuitry is further configured to generate data related a blood analyte level measurement based at least on a portion of the processed detector signals; and
the telemetry transmission portal is configured to transmit the data related to the blood analyte level to the external receiver.

24. The implantable analyte sensor of claim 19, wherein:
the at least one detector comprises a plurality of detectors; and
the detector array further comprises at least one electrolyte layer, at least a portion of the at least one electrolyte layer disposed between the plurality of detectors and the at least one membrane layer.

25. The implantable analyte sensor of claim 24, wherein the membrane structure further comprises: (i) a bottom wall, (ii) a top wall opposing the bottom wall, (iii) at least one side wall connected to each of the bottom wall and the top wall, the bottom wall, the top wall and the at least one side wall defining the cavity, the aperture disposed in the top wall.

26. The implantable analyte sensor of claim 25, wherein the bottom wall of the membrane structure is disposed between the at least one electrolyte layer and the enzymatic material.

27. The implantable analyte sensor of claim 19, wherein:
the implantable analyte sensor is configured for detection of blood glucose; and
the enzymatic material comprises a crosslinked protein material having at least two types of enzyme co-immobilized therein, the at least two types of enzyme comprising at least glucose oxidase (GO) and catalase.

28. The implantable analyte sensor of claim 27, wherein the glucose oxidase is immobilized within the crosslinked protein material at a first concentration, and the catalase is immobilized within the cross-linked protein material at a second concentration, the first concentration selected for a desired detector response time characteristic, the second concentration selected to be in excess relative to the first concentration in order to limit degradation of the glucose oxidase caused by exposure to a hydrogen peroxide byproduct produced during a reaction between the glucose oxidase and the blood glucose when the implantable analyte sensor is implanted subcutaneously.

29. The implantable analyte sensor of claim 19, wherein the at least one membrane layer comprises one or more three-dimensional portions which protrude above an outer surface of the biocompatible hermetically sealed housing, the one or more three-dimensional portions configured to promote interlock with the tissues of the body when the implantable analyte sensor is implanted subcutaneously.

30. The implantable analyte sensor of claim 29, wherein each of the one or more three-dimensional portions comprises at least an outer surface of the least one membrane layer, at least a portion of the outer surface comprising a textured surface.

31. The implantable analyte sensor of claim 30, wherein at least one of the one or more three-dimensional portions comprises a disc-shaped membrane structure, the disc-shaped membrane structure having a diameter that is greater than a height thereof.

* * * * *